US010502734B2

(12) United States Patent
Tamayo de Miguel et al.

(10) Patent No.: US 10,502,734 B2
(45) Date of Patent: Dec. 10, 2019

(54) SYSTEM FOR BIODETECTION APPLICATIONS

(71) Applicant: CONSEJO SUPERIOR DE INVESTIGACIONES CIENTIFICAS, Madrid (ES)

(72) Inventors: Francisco Javier Tamayo de Miguel, Madrid (ES); Priscila Monteiro Kosaka, Madrid (ES); Valerio Pini, Madrid (ES); Montserrat Calleja Goméz, Madrid (ES); Jose Jaime Ruz Martinez, Madrid (ES); Daniel Ramos Vega, Madrid (ES); Maria Ujue Gonzalez Sagardoy, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 116 days.

(21) Appl. No.: 15/315,029

(22) PCT Filed: Jun. 2, 2015

(86) PCT No.: PCT/ES2015/070434
§ 371 (c)(1),
(2) Date: Nov. 30, 2016

(87) PCT Pub. No.: WO2015/185778
PCT Pub. Date: Dec. 10, 2015

(65) Prior Publication Data
US 2017/0205405 A1 Jul. 20, 2017

(30) Foreign Application Priority Data

Jun. 3, 2014 (ES) .................................. 201430846

(51) Int. Cl.
| *G01N 21/552* | (2014.01) |
| *G01N 33/543* | (2006.01) |
| *G01N 21/65* | (2006.01) |
| *G01N 21/77* | (2006.01) |
| *G01N 21/47* | (2006.01) |
| *G01N 21/59* | (2006.01) |

(52) U.S. Cl.
CPC ....... *G01N 33/54346* (2013.01); *G01N 21/47* (2013.01); *G01N 21/554* (2013.01); *G01N 21/59* (2013.01); *G01N 21/658* (2013.01); *G01N 21/77* (2013.01); *G01N 21/7703* (2013.01); *G01N 33/54373* (2013.01); *G01N 2021/5903* (2013.01)

(58) Field of Classification Search
CPC ....... G01N 33/54346; G01N 33/54373; G01N 21/77; G01N 21/59; G01N 21/47; G01N 21/658; G01N 21/554; G01N 21/7703; G01N 2021/5903
See application file for complete search history.

(56) References Cited

U.S. PATENT DOCUMENTS

| 6,514,767 B1 | 2/2003 | Natan |
| 2009/0147254 A1 | 6/2009 | Kirby et al. |
| 2010/0053598 A1 | 3/2010 | Kwon et al. |

FOREIGN PATENT DOCUMENTS

| WO | WO 2012061778 | * 10/2012 | ............... C12Q 1/68 |
| WO | 2014016465 A1 | 1/2014 | |

OTHER PUBLICATIONS

Washburn et. al. (Anal Chem. 2009;81,pp. 9499-9506).*
Chaudharry et. al. (Defense Science Journal, 2009; vol. 59, No. 6, pp. 634-641).*
Lee et. al. (Lab Chip 2009; 9, pp. 2686-2690).*
C. I.L. Justino et al., "Review of Analytical figures of merit of sensors and biosensors in clinical applications," Trends in Analytical Chemistry, vol. 29, No. 10, 2010, pp. 1172-1183.
T. A. Taton et al., "Scanometric DNA Array Detection with Nanoparticle Probes," Science 289, 1757 (2000), pp. 1756-1760.
R. Elghanian et al., "Selective Colorimetric Detection of Polynucleotides Based on the Distance-Dependent Optical Properties of Gold Nanoparticles," Science 277, 1078 (1997), pp. 1077-1081.
X. Fan, et al., "Sensitive Optical Biosensors for unlabeled targets: A review," ScienceDirect, Analytica Chimica Acta 620 (2008), pp. 8-26.
G. Zheng, et al., "Frequency Domain Detection of Biomolecules using Silicon Nanowire Biosensors," National Institute of Health, Nano Lett. 2010, 10(8), pp. 1-9.
J. Tamayo, et al., "Imaging the Surface Stress and Vibration Modes of a Microantilever by Laser Beam Deflection Microscopy," Nanotechnology 23 (2012), pp. 1-8.
R. Jenison, et al., "Interference-based Detection of Nucleic Acid Targets on Optically Coated Silicon," Nature Biotechnology, vol. 19, Jan. 2001, pp. 62-65.
E. Stern, et al., "Label-free Biomarker Detection from Whole Blood," Nature Nanotechnology, vol. 5, Feb. 2010, pp. 138-142.
E. Goluch, et al., "A Bio-barcode Assay for On-chip Attomolar-sensitivity Protein Detection," Lab Chip, 2006,6, pp. 1293-1299.

(Continued)

*Primary Examiner* — Julie Wu
*Assistant Examiner* — Carmencita M Belei
(74) *Attorney, Agent, or Firm* — McNees Wallace & Nurick LLC

(57) ABSTRACT

The present invention relates to a system for biodetection applications comprising two basic elements, a substrate with a functionalized surface and a nanoparticle, the system being capable of enhancing the plasmonic effect of the nanoparticle. The invention also relates to a biosensor incorporating such system, in addition to the method for detecting and quantifying a target analyte selected in a sample using such system. Finally, the invention relates to a device which can detect the enhanced optoplasmonic effect of the nanoparticles by means of the system of the invention or by combining the detection of such optoplasmonic effect with the analysis of the changes in the mechanical characteristics in the substrate.

13 Claims, 12 Drawing Sheets

(56) References Cited

OTHER PUBLICATIONS

I. E. Tothill, "Biosensors for Cancer Markers Diagnosis," Seminars in Cell & Developmental Biology, 20 (2009), pp. 55-62.
J. Fritz, "Cantilever Biosensors," The Royal Society of Chemistry, Analyst, 2008, 133, pp. 855-863.
A. Boisen, et al., "Cantilever-like Micromechanical Sensors," Reports on Progress in Physics, 74, (2011), pp. 1-30.
J. Wang, "Amperometric Biosensors for Clinical and Therapeutic Drug Monitoring: A review," Journal of Pharmaceutical and Biomedical Analysis, 19, (1999), pp. 47-53.
P. D'Orazio, "Biosensors in Clinical Chemistry—2011 Update," Clinical Chimica Acta, 412, (2011), pp. 1749-1761.
R. Datar et al., "Cantilever Sensors: Nanomechanical Tools for Diagnostics," MRS Bulletin, 34, 2009, pp. 448-454.
"Carbon-Nanotube Based Electrochemical Biosensors: A Review," Department of Chemistry and Biochemistry, Electroanalysis, 2005, 17, No. 1, pp. 7-14.
O. Gnedenko, et al., "Highly sensitive detection of human cardiac myoglobin using a reverse sandwich immunoassay with a gold nanoparticle-enhanced surface plasmon resonance biosensor," Analytica Chimica Acta, 759, (2013), pp. 105-109.
Y. Bai, et al., "Aptamer/thrombin/aptamer-AuNPs sandwich enhanced surface plasmon resonance sensor for the detection of subanomolar thrombin," Biosensors and Bioelectronics, 47, (2013), pp. 265-270.
J. Martinez-Perdiguero, et al., "Surface plasmon resonance immunoassay for the detection of the TnFa biomarker in human serum," Talanta, 119, (2014), pp. 492-497.
J. Tamayo, et al., "Biosensors Based on Nanomechanical Systems," Chemical Society Reviews, 2013, vol. 42, pp. 1287-1311.
S. Ming et al., "Microcantilever Resonance-Based DNA Detection With Nanoparticle Probes," Applied Physics Letters, American Institute of Physics, vol. 82, No. 20, May 19, 2003, pp. 3562-3564.
K. Misiakos, "Monolithic Silicon Optoelectronic Devices for Protein and DNA Detection," SPIE, vol. 6125, 2006, pp. 6125W-1-61250W-1.
B. Wenger et al., "Au-Labeled Antibodies to Enhance the Sensitivity of a Refractometric Immunoassay: Detection of Cocaine," Biosensors and Bioelectronics, vol. 34, No. 1, Jan. 17, 2012, pp. 94-99.
A. Lukowiak et al., "Sensing Abilities of Materials Prepared by Sol-Gel Technology," Journal of Sol-Gel Science and Technology, Kluwer Academic Publishers, vol. 50, No. 2, Mar. 28, 2009, pp. 201-215.
Kosaka P., et al., "Simultaneous Imaging of the Topography and Dynamic Properties of Nanomechanical Sytems by Optical Beam Deflection Microscopy," Journal of Applied Physics, American Institute of Physics, vol. 109, No. 6, Mar. 24, 2011, pp. 64315-64315.
J. Wang, "Electrochemical Biosensors: Towards Point-of-Care Cancer Diagnostics," Biosensors and Bioelectronics, vol. 21, Nr: 10, pp. 1887-1892 (2006) (Abstract only).
Duan, X. et al., "Quantification of the Affinities and Kinetics of Protein Interactions Using Silicon Nanowire Biosensors," Nature Nanotechnology, vol. 7, Nr: 6, pp. 401-407 (2012).
M.C. Dixon, "Quartz Crystal Microbalance with Dissipation Monitoring: Enabling Real-Time Characterization of Biological Materials and Their Interactions," Journal of Biomolecular Techniques: JBT 19, p. 151 (2008).
K. Lange, et al., "Surface Acoustic Wave Biosensors: A Review," Analytical and Bioanalytical Chemistry, vol. 391, Nr: 5, pp. 1509-1519 (2008) (Abstract only).
C. O'Sullivan, et al., "Commercial Quartz Crystal Microbalances—Theory and Applications," Biosensors and Bioelectronics, vol. 14, pp. 663-670 (1999) (Abstract only).
J. Arlett, et al., "Comparative Advantages of Mechanical Biosensors," Nature Nanotechnology, vol. 6, Nr: 4, pp. 203-215 (2011).
A. Boisen, et al., "Design & Fabrication of Cantilever Array Biosensors," Materials Today, vol. 12, Nr: 9, pp. 32-38 (2009).
R. Raiteri., et al, "Micromechanical Cantilever-Based Biosensors," Sensors and Actuators B: Chemical, vol. 79, Nr: 2-3, pp. 115-126 (2001) (Abstract only).
P. S, Waggoner, et al., "Micro- and Nanomechanical Sensors for Environmental, Chemical, and Biological Detection," Lab Chip, vol. 7, pp. 1238-1255 (2007) (Abstract only).
K. Mayer, et al., "Localized Surface Plasmon Resonance Sensors," Chemical Reviews, vol. 111, Nr: 6, pp. 3828-3857 (2011) (Abstract only).
R. De La Rica, et al., "Plasmonic Elisa for the Ultrasensitive Detection of Disease Biomarkers with the Naked Eye," Nature Nanotechnology, vol. 7, Nr: 12, pp. 821-824 (2012).
J. Nam, et al., "Nanoparticle-Based Bio-Bar Codes for the Ultrasensitive Detection of Proteins," Science, vol. 301, Nr: 5641, pp. 1884-1886 (2003).
Dong et. al., "Two Types of Nanoparticle-Based Bio-Barcode Amplification Assays to Detect HIV-1 P24 Antigen," Virology Journal, vol. 9, Nr: 1, p. 180 (2012).
J. Storhoff, et al., "One-Pot Colorimetric Differentiation of Polynucleotides with Single Base Imperfections Using Gold Nanoparticle Probes," J. Am. Chem. Soc., vol. 120, pp. 1959-1964 (1998) (Abstract only).
P.S. Waggoner, et al., "Detection of Prostate Specific Antigen with Nanomechanical Resonators," Lab Chip, vol. , pp. 3095-3099 (2009).
P. R. Nair, et al., "Theory of "Selectivity" of Label-Free Nanobiosensors: A Geometro-Physical Perspective," Journal of Applied Physics, vol. 107, pp. 064701-064701-064706 (2010) (Abstract only).
P. Kosaka, et al., "Tackling Reproducibility in Microcantilever Biosensors: A Statistical Approach for Sensitive and Specific Endpoint detection of Immunoreactions," Analyst, vol. 138, pp. 863-872 (2013) (Abstract only).
M. Varshney, et al., "Prion Protein Detection Using Nanomechanical Resonator Arrays and Secondary Mass Labeling," Anal Chem. vol. 80, pp. 2141-2148 (2008).

\* cited by examiner

SYSTEM FOR BIODETECTION APPLICATIONS

FIELD OF THE INVENTION

The present invention belongs to the field of biosensors. More particularly, the present invention relates to a system for biodetection applications comprising two basic elements, a substrate with a functionalized surface and a nanoparticle, the system being able to enhance the plasmonic effect of the nanoparticle. The invention also relates to a biosensor incorporating such system, in addition to the method for detecting and quantifying a target analyte selected in a sample using such system. Finally, the invention relates to a device which can detect the enhanced optoplasmonic effect of the nanoparticles by means of the system of the invention or by combining the detection of such optoplasmonic effect with the analysis of the changes in the mechanical characteristics in the substrate.

BACKGROUND OF THE INVENTION

Biosensors

A biosensor measures the physical changes that a biological recognition layer bound to a solid transducer undergoes when it interacts with a sample containing targeted molecules. It therefore uses the capacity of some biomolecules (receptors) to specifically bind to (recognize) complementary biomolecules (ligands). The most typical interactions are complementary nucleic acid hybridization and antibody/antigen binding. Biosensors are increasingly sought after in fundamental biological studies, health sciences research, drug discovery and clinical diagnosis[1-3]. Depending on the measured physical change, biosensors can be classified as optical, electrical and mechanical biosensors.

Optical biosensors can mainly be divided into label-based detection and label-free detection. The most commonly used label-based biosensors are based on fluorescence-based detection; target molecules or biorecognition molecules are labeled with fluorescent labels, such as dyes; the intensity of the fluorescence signal indicates the amount of targeted molecules. Meanwhile, fluorescence-based detection is extremely sensitive and requires laborious labeling methods which can also interfere with the function of the biomolecule. In contrast, in label-free detection, the targeted molecules are not labeled or altered and are detected in their natural forms. A significant part of label-free optical sensors measures the refractive index change close to the sensor surface by exciting an evanescent field which exponentially decays into the bulk solution with a characteristic length between tens to hundreds of nanometers[4]. The surface plasmon resonance (SPR) method and localized surface plasmon resonance (LSPR) methods are the most popular among label-free optical biosensors.

Electrochemical devices have traditionally received the most attention among electrical biosensors[5-7]. These devices usually couple enzymes that produce or consume electrons upon substrate recognition to a transducer consisting of electrodes. Many of these enzymes specifically catalyze the reactions of clinically important analytes such as glucose, lactate, cholesterol, amino acids, urate, pyruvate, glutamate, alcohol, hydroxybutyrate, to name a few. Nanotechnology advances are also providing nanoscale electrical biosensors based on semiconductor nanotubes and nanowires, in which electrochemical gating occurs from a change in the local surface potential due to target binding[8-10].

The quartz crystal microbalance has become one of the most established techniques among mechanical biosensors[11-13]. These devices are based on quartz crystal resonators (such as those used in watches) which are piezoelectric and therefore allow directly measuring crystal deformation using electrical methods. In these devices, resonance frequency is measured and related to the change in mass induced by the analyte binding to the recognition layer immobilized on the crystalline surface. A subclass of mechanical biosensors is called nanomechanical biosensors which makes the best use of the nanoscale size of at least one of their dimensions[14-20].

Among the existing methods, the most satisfactory biosensors in the biomedical field include end-point detection bioassays such as ELISA. ELISAs are essential tools in the biomedical field due to their good sensitivity, assay simplicity, reliability and high performance.

On the other hand, devices such as lateral flow tests are of the utmost importance given the short analysis time needed and they have been satisfactorily miniaturized and simplified to the point that the test can even be done at home. However, the lowest analyte concentration which they can detect is usually up to 0.1 µM, which is not good enough for detecting many targets of biological importance. In comparison, ELISA requires a longer analysis time (~1 hour), but offers better concentration sensitivity (~1 pM).

The biodetection technique which can combine excellent sensitivity and specificity with a short analysis time, together with miniaturization potential, is still under research. Particularly, there is a high demand for techniques which can be integrated in a point-of-care device with credible sensitivity, quantification capacity and good dynamic interval. No technique providing same has been demonstrated until now. The capacity of being integrated in a point-of-care (POC) device means that detection protocols must be simple, small volumes of sample must be used and they must not require complicated preparation and/or washing steps or complex chemicals for preparing the samples and/or detection devices. A low cost for complete analyses and a long storage life also are requirements for obtaining a commercially viable product.

Nanoparticle-based Biosensors

There are approaches in the prior art that have been successful in many, although not all, of the challenges mentioned for POC devices. Use of nanoparticles (NPs) has played a role in this success. Particularly, gold nanoparticles and other noble metal nanoparticles have been used in analyte detection. The localized surface plasmon resonance (LSPR) in gold NPs shifts when the surrounding dielectric constant changes, such that shifts in the LSPR spectral peak facilitated by biomolecule binding provide a method for analyte detection in clinical samples. Different detection approaches using this phenomenon at a nanoscale are reviewed in reference 21.

In a satisfactory approach called plasmonic ELISA, the localized plasmon resonance shift facilitated by gold nanoparticle aggregation is used for coloring the detection label of very low concentrations of an analyte of interest. In reference 22, both PSA and the p24 antigen of the HIV-1 capsid are detected at concentrations of only $1\times10^{-18}$ g/ml. In this method, the biocatalytic cycle of an enzyme generates colored NP solutions due to the fact that aggregated NPs are formed when the hydrogen peroxide concentration decreases. Analyte binding promotes NP aggregation, which in turn gives a blue color to the solution. This color change is used as a detection signal which can even be tracked at a glance and thus provides a low cost detection approach.

In another relevant methodology, labeling NPs with various DNA sequences provides the multiplexing capacity that metal NPs alone would not have, since they lack a range of color labels for labeling each specific reaction. The so-called bio-barcode method has not only been used for DNA detection, but rather it has also been used satisfactorily for protein detection. The bio-barcode is based on magnetic microparticle probes with antibodies that bind specifically to a target of interest, for example, a clinically relevant protein such as a prostate-specific antigen (PSA) (see reference 23) and nanoparticle probes that are encoded with DNA that is unique to the target protein of interest and antibodies that can sandwich the target captured by the microparticle probes. Magnetic separation of the complexed probes and target, followed by dehybridization of the oligonucleotides on the nanoparticle probe surface allows determining the presence of the target protein by identifying the oligonucleotide sequence released from the nanoparticle probe. Due to the fact that the nanoparticle probe carries with it a large number of oligonucleotides for the protein binding event, there is substantial signal amplification and the target protein can be detected at low concentrations (30 attomolar concentration). Alternatively, a polymerase chain reaction (PCR) in the oligonucleotide barcodes can boost the sensitivity to 3 attomolar. Comparable clinically accepted conventional assays have sensitivity limits of 3 picomolar, six orders of magnitude less sensitive than that observed with this method[23]. A limitation of this technique is the analysis time required, up to 100 minutes, given the need to separate the complexed probes and target from the sample solution and then identify the DNA labels. Quantification is also possible with this method. One approach is to perform PCR and/or gel electrophoresis, but these are methods that are not suitable for point-of-care applications and exclude the rapid analysis described in reference 25.

An alternative detection method is based on the scattered light spectral change when at least two NPs are placed close to one another[26,27]. The color change is due to a shift in the surface plasmon resonance of Au nanoparticles when at least two NPs are placed close to one another. This produces a detectable color shift and a change in the collected light intensity which can be measured optically. NP probe complexes always comprise two or more nanoparticles bound to a specific target analyte; this has been referred to as a light scattering complex. This has the advantage that only NP aggregates containing the analyte are detected. Non-aggregated particles, including those not containing the target analyte, are not detected in this method. This allows detecting NP aggregates in the presence of a significant excess of non-aggregated particles. This method has demonstrated excellent sensitivity, better than 10 femtomoles of an oligonucleotide. Within this method, use of evanescent illumination by means of a supporting waveguide and scatter-based colorimetric detection has been demonstrated to be 4 orders of magnitude better than absorbance-based spot tests (patent document EP1639370).

One way to eliminate the need for PCR amplification while at the same time maintaining a good multiplexing capacity is to hybridize GNP scattering complexes on a solid support functionalized with known sequences in defined positions, as is done in fluorescent arrays. Subsequent scanometric detection of the scattered light serves as a biosensing signal and the multiplexing capacity is obtained through the predefined positions of the known immobilized sequences. A way to amplify this optical signal is usually needed. A method for amplifying the scattered light signal of NP labels is the silver reduction promoted by nanoparticles[28] or colorimetric response by enzyme catalysis on optically coated silicon substrates[29]. This method is used for amplifying the optical signal and also allows quantifying the amount of analyte in the sample[30].

Nanomechanical Resonators-based Biosensors

Nanomechanical resonators have demonstrated unprecedented limits of detection in the mass detection of atoms and molecules in vacuum. The mass limits of detection have been recently pushed down to the yoctogram range, i.e., the mass of a single proton can be measured. Two components are essential to achieve mass sensitivity: devices with nanoscale dimensions and high quality factors (1000-100000) that imply measurements in vacuum. However, biomolecule detection must ideally be carried out in aqueous solutions, the natural environment in which biological processes occur. Nanomechanical resonators in liquids show a very low quality factor (1-10) as a result of viscous damping. Furthermore, the liquid is entrained along with the nanomechanical resonator, increases its effective mass and thus reduces the sensitivity. Miniaturization of the devices to the nanoscale does not improve these limitations. More importantly, biological detection requires many repetitive measurements that can only be achieved with disposable and cost/effective devices that can be easily both handled and measured. These requirements are fulfilled by commercially available microcantilever arrays, but not by the nanoscale mechanical resonators of the state of the art that are still manufactured at a low rate by nanofabrication techniques and are highly irreproducible in the dimensions and mechanical response. Furthermore, measurement of the resonant frequency of these devices in liquid is scientifically and technically challenging. These limitations have limited the success of nanomechanical resonators as biological sensors.

Nanomechanical Resonators with Mass Labels

Nanomechanical resonators have used NPs for amplifying the signal; herein, greater mass binding provided by the labels increases sensor mechanical response. Herein, reduction in the resonance frequency is related to the added mass of the analyte-NP complex which binds to the resonator. Despite the fact that dynamic nanomechanical sensors have demonstrated a good performance without labels, labeling greatly improves specificity and can reduce the limit of detection. It has been demonstrated that sample labeling for nanomechanical detection is advantageous in end-point assays. Craighead et al. demonstrated in reference 31 that labeling a monoclonal antibody with nanoparticles in a sandwich-type immunoassay improved the limit of detection by three orders of magnitude to reach 2 ng/ml in prion protein detection and to even detect the presence of 50 fg/ml of enriched PSA in a background noise of fetal bovine serum. The technique is also quantitative since the authors found a clear linear dependence of the frequency response on PSA concentration. The capacity for detecting fM concentrations of a target protein in a realistic background noise places labeled resonant cantilever sensors in an excellent position for competing with the other innovative techniques mentioned, in addition to more established technologies. Nevertheless, nanomechanical resonators are still not widely used in clinical practice. That is due to the fact that they lack the necessary robustness in response. The few studies showing a statistically significant number of tests show that the number of false positives and false negatives is still too high. The frequency shift commonly used as detection signal in these sensors depends largely on the non-specific adsorption on the device surface.

A key limitation of nanomechanical resonators is non-specific adsorption. The final limits of detection predicted by theoretical approaches can be far from the actual limits of detection when nanomechanical biosensors functionalized with bioreceptors are immersed in complex solutions, such as serum, for detecting the presence of biomarkers in real time or ex-situ. In this situation, other molecules at a much higher concentration, even trillions of times higher, are present in the solution. Although these molecules have lesser affinity for the receptors grafted with sensors, their high concentration confers the actual limit of detection. For example, cancer biomarkers are in blood plasma at a concentration in the range of 1 ng/ml, whereas the concentration of undesired proteins is about 70 mg/ml. Most nanomechanical biosensors meet the sensitivity for achieving cancer biomarker detection. However, the selectivity determining the false positive and false negative rates has received little attention. Cancer marker detection in complex media such as serum requires selectivity greater than 1 part per million.

Theoretical predictions indicate that the selectivity required for biomarker detection in complex media can be achieved by functionalizing the sensors with a high surface receptor density[32]. This prediction is according to the findings in surface tension-based nanomechanical biosensors, in which the best results are obtained at high receptor packing densities. A second theoretical prediction is that the step of additional intermediate surface passivation by small inert molecules after receptor incubation could significantly reduce biofouling and aid in achieving better selectivity. Interestingly, the size and geometry of the blocking molecule used to refill the empty spaces on the sensor surface plays a critical function. That is according to the recent statistical analysis results of the effect of immunoreactions on nanomechanical biosensor response in the static mode[33]. The study comprised 1012 cantilevers with different antibody surface densities, two blocking strategies based on polyethylene glycol (PEG) and bovine serum albumin (BSA), meticulous controls with non-specific antibodies and small proteins such as lysozymes. The study showed that the performance of the assay depends critically on both the antibody surface density and the blocking strategies. It was found that optimal conditions involve antibody surface densities near but below saturation and blocking with PEG.

Furthermore, other practical approaches for minimizing non-specific adsorption and enhancing selectivity has been proposed. Use of arrays of nanomechanical elements with an internal reference aids in rejecting common noise sources, including non-specific adsorption. Another approach is the implementation of the sandwich assays conventionally used in ELISA. In this assay, the nanomechanical system is functionalized with a molecular receptor specific for the biomarker of interest. After exposure of the nanomechanical system to the sample, the device is incubated with secondary receptors bound to a molecule or a material acting as a signal amplifier, such as a nanoparticle, for increasing the mass effect. Use of two different receptors greatly enhances sensitivity and specificity. This approach was applied for detecting prion proteins with nanomechanical resonator, which in conformationally altered forms are known to cause neurodegenerative diseases in animals as well as human beings[34]. The resonance frequency was detected ex situ in high vacuum. For the direct incubation of the nanomechanical resonators functionalized with a primary antibody against the prion protein, the limit of detection was about 20 µg/ml. When the resonators were subjected to a subsequent step of incubation with bound secondary antibodies, the limit of detection was enhanced 3 orders of magnitude, being about 2 ng/ml.

A second promising strategy that maintains the natural label-free characteristic of nanomechanical biosensors is to implement microfluidics for sample purification and preconcentration. The potential of this approach has been demonstrated with label-free nanowire nanosensors. In this work, a microfluidic purification chip simultaneously captures multiple biomarkers from blood samples and releases them, after washing, into purified buffer for detection by nanosensors[8]. This two-stage approach isolates the detector from the complex environment of whole blood, and reduces its minimum required sensitivity by effectively pre-concentrating the biomarkers. The authors demonstrated quantitative and specific detection of two model cancer antigens from a 10 ml sample of whole blood in less than 20 min.

Although nanotechnology has provided biosensors with unpredictable sensitivity levels without the need of labeling, nanosensors have also shown significant difficulties in issues relating to specificity and reproducibility, and they are therefore still not ready for biomarker selection in blood. This arises from the extreme difficulty in 'finding' low-abundance protein biomarkers in a 'haystack' of plasma proteins, some of them at concentrations at least seven orders of magnitude higher (albumin about 40 mg/ml). Therefore, the situation is that the high biological noise perceived by non-specific interactions greatly exceeds the intrinsic noise of most existing nanosensors. In short, the problem is not sensitivity, but rather:

Specificity, for discriminating traces of biomarkers in the complex blood protein mixture.

Reliability, for minimizing distressing false positives and false negatives in patient diagnosis.

The authors of the present invention have now found a system for biodetection applications which allows ultra-low limits of detection since it discriminates concentrations around 10 ag/ml. Furthermore, the system allows target analyte detection in complex biological background noises, such as for example, blood samples, without needing any purification step. The invention is based on a sandwich-type optical assay which takes advantage of the surprising and unexpected enhancement of the plasmonic effect caused in the nanoparticles by the combination of the particular nature and design of the substrate used in the biosensor and the particular nature and dimensions of the nanoparticle. This system can be adapted in a nanomechanical device for the purpose of analyzing both optoplasmonic and mechanical signals such that it improves detection reliability. The robustness of this dual biosensor leads to extremely low false positive and false negative rates, $\approx 2\times 10^{-4}$ at an ultra-low concentration of 100 ag/ml, thereby providing an excellent solution for being integrated in a POC device.

DESCRIPTION OF THE INVENTION

The following definitions are provided to aid in the understanding and interpretation of the present invention:

Biosensor: An analytical device comprising a biological recognition element (for example, enzyme, receptor, DNA, antibody, or microorganism) in close contact with a transducer of electrochemical signals, mechanical signals, optical signals, thermal signals, acoustic signals or other physical signals which, in combination, allow chemical property analysis or target analyte detection or quantification.

Dielectric material: A dielectric material is an electric insulator which can be polarized by an applied electric field.

Functionalized surface or surface functionalization: A method or technique for introducing chemical functional groups on a surface. The latter is used in biosensors for immobilizing a recognition element on a surface, in the present invention, on the substrate surface.

Recognition element: It is the immobilized element of the system which functionalizes the substrate surface and can recognize and specifically bind to the target analyte. The recognition element can be selected from, but is not limited to, an antibody, a receptor, a peptide, a protein, a carbohydrate, a nucleic acid, a cell, a microorganism or a part thereof.

Detection element: It is the element of the system bound to the nanoparticle which can recognize and specifically bind to the target analyte. The detection element together with the nanoparticle allow target analyte detection when it is present in the sample.

Target analyte: It is the element sought for detection and/or quantification. It can be of any nature such as organic or inorganic molecules (drugs, hormones, cholesterol, etc.), biological molecules (peptides or proteins, nucleic acid molecules, growth factors, biomarkers etc.), cells (protozoan cells, bacterial cells, fungal cell, eukaryotic cells) or cell fragments (bacterial walls, cell organelles such as mitochondria, cell vesicles, etc.) or viruses.

Extinction coefficient: The extinction coefficient is the imaginary part of the complex refractive index.

Refractive index: The refractive index of a substance (optical medium) is a dimensionless number describing how the light or any other radiation propagates through that medium.

Surrounding material: It is the material under both substrate surfaces in the system of the invention. The refractive index of the surrounding material is relevant for achieving enhanced plasmonic effect.

Plasmonic effect: It is the phenomenon produced in nanoparticles having plasmonic properties when they are irradiated with a suitable electromagnetic radiation. The plasmonic effect is produced by free electron oscillations induced in a metal by an electromagnetic wave.

Antibody: A Y-shaped protein (immunoglobulin) on the surface of B lymphocytes which is secreted into the blood or lymph in response to an antigenic stimulus, such as a bacterium, virus, parasite or transplanted organ, and which neutralizes the antigen by binding specifically to it. The antibody-antigen pair formation can be detected by several methods and it is the basis of many biosensors.

Receptor: It is a biological structure which can detect chemical stimuli of its surroundings. Receptors are usually present on the cell surface and are suitable for detecting a particular type of molecule which is responsible for inducing a response in the cell once in contact with the receptor.

Peptide: Short chains of amino acid monomers bound by peptide bonds.

Carbohydrate: In the context of the invention, it refers to complex oligosaccharide or polysaccharide molecules having the capacity to bind to specific targets. Lipopolysaccharide can be mentioned as an example.

Nucleic acid: Any polymeric or oligomeric molecule having a backbone containing a sequence of nitrogenous bases—adenine (A), thymine (T), cytosine (C) and guanine (G). In the context of the present invention, nucleic acid molecules include, among others, DNA molecules, RNA molecules, aptamers or PNA molecules.

Nanoparticle of plasmonic metamaterial: It is a nanoparticle made of an artificial material manipulated to show plasmonic properties.

Transmittance: Transmittance is the fraction of incident light (electromagnetic radiation) at a specified wavelength going through a sample.

Reflectance: Reflectivity or reflectance is the fraction of incident electromagnetic power which is reflected from a separating surface.

Detection: It is the action of identifying the presence or absence of the target analyte in the sample.

Quantification: It is the action of determining the concentration of a target analyte in the sample.

Sample: A biological fluid preparation that will be analyzed usually in liquid form although it can also be in solid form which will be resolved into liquid form or can be reconstituted.

Electromagnetic radiation: Electromagnetic radiation is a fundamental phenomenon of electromagnetism, behaving like waves propagating through space and carrying radiant energy. An electromagnetic wave has both electric and magnetic field components which oscillate in a fixed ratio with respect to one another, are perpendicular to one another and perpendicular to the energy and wave propagation direction.

Light scattering: Light scattering is a type of interaction between the material and an electromagnetic wave. When a propagating wave strikes a surface, the reflected wave is usually concentrated in the specular direction as determined by the well-known laws of reflection. In addition to specular reflection, there is also a diffuse component which is irradiated on a large range of angles centered on the specular beam which is commonly known as light scattering. Scattering methods can be produced from non-zero surface roughness or through the presence of small particles deposited on the surface.

Absorption: Electromagnetic radiation absorption is the form in which the energy of electromagnetic radiation is gathered by the material, usually the electrons of an atom. Therefore, the electromagnetic energy is transformed into internal energy of the absorber, for example, thermal energy.

Extinction signal: The term "extinction" means the loss of light in a transmitted optical beam when it goes through a medium or object. Two different mechanisms contribute to extinction: absorption and scattering.

A first objective of the invention relates to a system for biodetection applications comprising:
  a. a substrate of dielectric material having at least one surface functionalized with a recognition element which can bind specifically to a target analyte and
  b. at least one nanoparticle with plasmonic properties which comprises at least one detection element bound thereto and which can bind specifically to the target analyte in a sandwich-type arrangement,
characterized in that:
  the substrate of dielectric material has a thickness between 0.1 µm and 5 µm and an extinction coefficient less than 0.3,
  the nanoparticle has at least one of its dimensions with a size of 2 nm to 300 nm, and
  in that the ratio between the refractive index of the dielectric material and the surrounding material is greater than 1.1.

The system of the invention is suitable for sandwich-type detection and quantification methods (see, for example, FIG. 1). Use of a recognition element and a detection element is a first aspect greatly improving the sensitivity and specificity of the system. However, the most surprising and advantageous aspect of the system of the invention is derived from the enhanced plasmonic effect which can be achieved in optoplasmonic detections. This particular effect allows ultra-low limits of detection. The effect is a hybrid plasmonic mode resulting from the combination of the particular nature and design of elements forming the system, specifically the substrate and the nanoparticle.

The substrate must be a dielectric material such that the surface plasmon resonance phenomenon can take place. Any dielectric material in the electromagnetic spectral range of interest is suitable in the system of the invention. The only condition is that the extinction coefficient thereof must be less than 0.3. In a particular embodiment, the dielectric material is quartz, silicon, silicon nitride, silicon carbide, graphene, polymers such as photoresists, for example SU8, and hydrogels such as mixtures of PEG and PLA or of DEXTRAN and PEG. The most preferred dielectric materials are silicon or silicon nitride.

Another important aspect of the system of the invention is the substrate design. There are two key points in the substrate design that must be complied with in order to achieve the enhanced plasmonic effect in the nanoparticle site.

The first key point is that the thickness of the substrate must be between 0.1 µm and 5 µm, more preferably between 0.25 µm and 2 µm. For greater thicknesses, the incident electromagnetic radiation is refracted and cannot produce a multi-reflection effect within the substrate cavity which is the physical phenomenon which ultimately contributes to producing plasmonic effect enhancement (see FIG. 2a). In practice, plasmonic effect enhancement is a hybrid mode resulting from the coupling of the localized surface plasmon mode on nanoparticles and the optical cavity mode. When the nanoparticle is on the substrate, in addition to backscattering, several pathways aid in enhancing scattering by a single nanoparticle. One pathway involves forward scattering amplification by the nanoparticle by multiple reflections. In this mechanism, the coupling between the dipolar plasmon resonance of the nanoparticle and the resonances of optical substrate cavities creates a hybrid mode which strengthens the scattering signal in the nanoparticle site. In a second pathway, the unscattered light experiences multiple reflections in the substrate optical cavity, producing a cascade of scattering interactions in the neighboring nanoparticle sites leading to a greater apparent density of nanoparticles in a dark-field image, for example.

The importance of thickness in the scattering signal is clearly demonstrated by a particular embodiment of the invention in which the substrate is in the form of a cantilever with a design having a thickness between 0.1 µm and 5 µm. A clear difference can be observed in the scattering signal intensity between the chip region in which the thickness is greater than 5 µm and the cantilever region in which the thickness is between 0.1 µm and 5 µm (see FIG. 6a).

The second key point to be taken into account in the design of the system is that the ratio between the refractive index of the dielectric material (substrate) and the surrounding material must be greater than 1.1. This aspect is also essential in achieving the multi-reflection effect in the substrate cavity. The presence of surrounding materials surrounding the substrate which have a different refractive index in the particular ratio greater than 1.1 means that the opposite surfaces of the substrate are like mirrors, allowing multi-reflection within the cavity. The surrounding material can be both in the solution itself in which the substrate is immersed for the detection and any surrounding fluid or gases, or a particular solid surrounding material with the only condition that the refractive index of the surrounding material is different from the refractive index of the substrate.

In principle, the system of the invention can be used in any type of biosensor or mechanical resonator formation. Particularly, in the system of the invention the substrate can be in the form of a microcantilever, a micropillar, a string, a trampoline, a rectangular cantilever, a triangular cantilever, a pyramidal cantilever, a blade cantilever, a membrane, a plate, a bridge, a hollow tube or a nanowire (see, for example, FIG. 11).

The target analyte is the element that will be detected from the sample, particularly from biological samples. The target analyte can be of any nature such as organic or inorganic molecules (drugs, hormones, cholesterol, etc.), biological molecules (peptides or proteins, nucleic acid molecules, growth factors, biomarkers etc.), cells (protozoan cells, bacterial cells, fungal cell, eukaryotic cells) or cell fragments (bacterial walls, cell organelles such as mitochondria, cell vesicles, etc.) or viruses.

An advantage of the system of the invention is that it allows detecting and quantifying analytes with complex samples, such as for example, blood or urine samples, without needing any purification step or separation step. This makes the handling simpler and reduces the time for detection, which means that the present system is very suitable for implementation in POC devices.

The recognition element functionalizing the substrate surface can be any element which can recognize and bind specifically to a target analyte. In this sense, the recognition element can be an antibody (a polyclonal or monoclonal antibody), a receptor (a cell surface receptor such as an opioid receptor), a peptide (such as an opioid peptide), a protein (such as lectins), a carbohydrate (such as lipopolysaccharide O-antigen), a nucleic acid (a DNA or RNA sequence), a cell (protozoan cells, bacterial cells, fungal cell, eukaryotic cells), a microorganism or a part thereof (such as bacterial walls, cell organelles such as mitochondria, cell vesicles, etc). In a preferred embodiment of the invention, the recognition element is an antibody, more preferably a monoclonal antibody.

The other essential feature of the system, besides the functionalized substrate, is the nanoparticle. The nanoparticle must naturally have plasmonic properties. In principle, any type of nanoparticle with plasmonic properties can be used. Therefore, the nanoparticle can be, for example, a gold nanoparticle, a silver nanoparticle or a nanoparticle of plasmonic metamaterial such as, but not limited to, titanium nitride and non-stoichiometric oxides such as non-stoichiometric vanadium, titanium and aluminum oxides.

Furthermore, the nanoparticle can adopt a plurality of forms or structures, such as for example, nanospheres, nanorods, pointed nanorods, nanoshells, nanocages/frames, hollow nanospheres, tetrahedra, octahedra, cubes, icosahedra, rhombic dodecahedra, concave nanocubes, tetrahexahedra, obtuse triangular bipyramids, trisohectahedra and nanoprisms (see FIG. 12), but it is essential that at least one of its dimensions has a size of 2 nm to 300 nm, preferably 5 nm to 150 nm, because the plasmonic resonance peak is highly dependent on the nanoparticle size.

The nanoparticle comprises at least one detection element bound thereto which can bind specifically to the target analyte. The detection element can be any type of element which can bind to the target analyte, therefore, in principle its nature can be the same as or similar to that of the recognition element. However, in a preferred embodiment the detection element is selected both from an antibody and from a nucleic acid molecule. The function of the detection element is to detect the presence of the target analyte captured by the recognition element immobilized on the substrate surface. Therefore, the nanoparticle will only bind to the substrate by means of the detection element bound thereto if the target analyte is present in the analyzed sample. In such case, the recognition element can bind to the target analyte which is then detected by the detection element in a sandwich-type arrangement. The absence of the target analyte in the sample results in the recognition element not binding to the target analyte and therefore, detection by the detection element not occurring.

In summary, if the target analyte is present in the sample, even at ultra-low concentrations, it can be detected and quantified based on the scattering intensity or extinction intensity (depending on the measured parameters) produced by the nanoparticles. If the target analyte is not present in the sample, there would be no detectable plasmonic effect on the substrate since nanoparticles will not be present.

The detection and quantification can be performed by measuring the scattering intensity produced by the nanoparticles when the system is irradiated with electromagnetic radiation. There would be a detectable plasmonic effect due to irradiation at any wavelength of the white light spectrum as a result of the amplification of the signal provided by the substrate which complies with the design parameters.

If the type of measured signal is the scattering signal, the measurement is taken in reflectance and, in such case, the reflectance index of the substrate is comprised between 0.01 and 1.

The detection and quantification can alternatively be carried out by measuring the extinction signal of the nanoparticles irradiated with electromagnetic radiation. If the extinction signal is measured, the measurement is taken in transmittance and, in such case, the transmittance index of the substrate is comprised between 0.01 and 1.

The nanoparticles in the system of the invention can be viewed through optical means such as a dark-field microscope or a cross-polarization microscope.

An additional aspect of the invention is a biosensor comprising a system according to the invention. In principle, the system of the invention is applicable to any type of biosensor on which the system can be arranged.

In a particularly preferred embodiment, the system is arranged in a micro or nanomechanical biosensor such that optomechanical-plasmonic signals can be detected and analyzed. This particular type of dual biosensor allows greater reliability since the response of the biosensor is only considered positive when both the plasmonic and mechanical signals give a positive result. Although the dual biosensor does not improve the limit of detection of the optoplasmonic system of the invention alone, it clearly improves assay specificity, thereby improving assay reliability.

For example, in a particular embodiment of a substrate-based dual signal biosensor in the form of a microcantilever in which both the plasmonic and mechanical signals were measured, it was observed that the error rate for lower concentrations was smaller in optoplasmonic transduction. For higher concentrations at 1 fg/ml, the error rate of both optoplasmonic and mechanical transductions was again comparable, but positively, the combination of optoplasmonic and mechanical signals (optomechanical-plasmonic signal) significantly enhanced assay reliability leading to extremely low false positive and false negative rates, of about $2 \times 10^{-4}$, at an ultra-low concentration of 100 ag/ml of the target analyte (FIG. 10).

In a particular embodiment, the biosensor is arranged in the form of an array comprising multiple systems according to the invention, each system comprising a substrate designed for detecting a different target analyte or different concentrations of the same analyte.

Another aspect of the invention is a method for detecting and/or quantifying a target analyte selected in a sample which comprises:
  a) contacting a sample with a substrate of dielectric material having a surface functionalized with a recognition element which can bind specifically to the target analyte, the substrate of dielectric material having a thickness between 0.1 μm and 5 μm and an extinction coefficient less than 0.3 and the ratio between the refractive index of the dielectric material and the surrounding material being greater than 1.1
  b) adding to the substrate resulting from a) at least one nanoparticle with plasmonic properties and having at least one of its dimensions with a size of 2 nm to 300 nm, which comprises at least one detection element bound thereto and which can bind specifically to the target analyte, for the purpose of detecting the presence of the target analyte bound to the recognition element
  c) irradiating the substrate resulting from b) with electromagnetic radiation in which the presence of the target analyte in the sample produces a plasmonic effect in the nanoparticles amplified by the presence of the substrate which can be detected by optical means,
  d) measuring light scattering or extinction signal intensity such that it detects the presence or absence of the target analyte in the sample and for the quantification thereof.

The method of the invention is based on using the sandwich-type detection system of the invention as described above.

Step a) is the recognition step in which the sample is contacted with the functionalized substrate surface. The substrate surface is designed for detecting a particular type of target analyte. Therefore, after a suitable incubation time such that the reaction can take place if the target analyte is present in the sample, it will bind to the recognition element and will therefore be immobilized on the surface.

As described above, the dielectric material used in the method can be any dielectric material as long as it has an extinction coefficient less than 0.3. In a particular embodiment, the dielectric material is quartz, silicon, silicon nitride, silicon carbide, graphene, polymers such as photoresists such as SU8 and hydrogels such as mixtures of PEG and PLA or of DEXTRAN and PEG. The most preferred dielectric materials are silicon or silicon nitride.

Also as described above, the recognition element used in the method of the invention can be any element which can recognize and bind specifically to a desired target analyte. In this sense, in a particular embodiment the recognition element can be an antibody (a polyclonal or monoclonal antibody), a receptor (a cell surface receptor such as an opioid receptor), a peptide (such as an opioid peptide), a protein (such as lectins), a carbohydrate (such as lipopolysaccharide O-antigen), a nucleic acid (a DNA or RNA sequence), a cell (protozoan cells, bacterial cells, fungal cell, eukaryotic cells), a microorganism or a part thereof (such as bacterial walls, cell organelles such as mitochondria, cell vesicles, etc). In a preferred embodiment of the invention, the recognition element is an antibody, more preferably a monoclonal antibody.

Step b) of the method of the invention comprises the detection step. The nanoparticle acting as a label for detection and quantification is bound to a detection element which can bind specifically to the target analyte in a different position or area of the recognition element. If the target analyte is present in the sample, the structure resulting from step a) will be detected by the detection element after a suitable incubation time. Once the detection reaction has taken place, the nanoparticles are immobilized on the substrate surface and are in the condition of being detected and/or quantified based on their plasmonic properties.

The detection element bound to the nanoparticle used in the context of the method can be any type of element which can bind to the target analyte, therefore, in principle, its nature can be the same as or similar to that of the recognition element. However, in a preferred embodiment the detection element is selected both from an antibody and from a nucleic acid molecule.

Also as described above, the type of nanoparticle used in the method of the invention can be any nanoparticle having plasmonic properties. In this sense, the nanoparticle can be a gold nanoparticle, a silver nanoparticle or a nanoparticle of plasmonic metamaterial. With respect to the shape, the nanoparticle can adopt any structure such as nanospheres, nanorods, pointed nanorods, nanoshells, nanocages/frames, hollow nanospheres, tetrahedra, octahedra, cubes, icosahedra, rhombic dodecahedra, concave nanocubes, tetrahexahedra, obtuse triangular bipyramids, trisohectahedra and nanoprisms as long as one of its dimensions has a size of 2 nm to 300 nm.

Step c) comprises irradiating the substrate surface with electromagnetic radiation such that it shows the presence or absence of the nanoparticle in the substrate. The incident electromagnetic radiation on the substrate resulting from step b) will show whether or not the sample contains the target analyte. If the target analyte is present in the sample, the incident electromagnetic radiation will produce a plasmonic effect in the nanoparticle that will be greatly enhanced by the particular phenomena taking place within the substrate cavity due to its particular design. As described above, the enhanced plasmonic effect produced when the nanoparticles are present in the substrate is a hybrid mode resulting from the coupling of the localized surface plasmon mode on nanoparticles and the optical cavity mode.

The last step of the method of the invention, step d), comprises measuring light scattering or extinction signal intensity such that the presence or absence of the target analyte in the sample is detected and for the quantification thereof. The measurements can be made using optical devices or means suitable for such task such as a dark-field microscope or a cross-polarization microscope.

The quantification can be performed based on the light scattering signal intensity or the light extinction signal intensity. The measured signal intensity can be linked to an unknown analyte concentration by comparing with a calibration curve obtained from samples with previously known analyte concentrations.

The method of the invention can be designed for measuring the enhanced plasmonic effect on the nanoparticles in reflectance or transmittance.

If the measurement is taken in reflectance, then the scattering signal intensity is measured and the substrate of dielectric material must therefore have a reflectance index comprised between 0.01 and 1.

Alternatively, if the measurement is taken in transmittance, then the extinction signal intensity is measured and the substrate of dielectric material must therefore have a transmittance index comprised between 0.01 and 1.

The method of the present invention allows ultra-low limits of detection since it discriminates concentrations around 10 ag/ml and has the advantage that it allows target analyte detection in complex biological samples such as blood or urine samples without needing any prior sample preparation or purification.

In a particularly preferred embodiment, the method of the invention is performed in a micromechanical system whereby the substrate of dielectric material is arranged as a mechanical element which can experience change in at least one mechanical characteristic when the target analyte is present in the sample, and when the following additional steps are performed:

e) measuring the at least one mechanical characteristic in the mechanical element such that it detects the presence or absence of the target analyte in the sample, f) combining the optical data obtained in step d) with the mechanical data of step e) in order to improve the reliability of the detection method.

The inventors have found that in this particularly preferred embodiment, although the method of the invention does not significantly improve the limit of detection, it improves the reliability of the method when compared with the method based on optoplasmonic effect alone. The method of the invention in this particularly preferred embodiment leads to very low false positive and false negative rates. The greater reliability is explained due to the fact the result of the method is only considered when both the plasmonic and mechanical signals give a positive result.

In this particular embodiment, the substrate of dielectric material which is essential in the present invention due to its optical properties is arranged so that it also acts as a mechanical element which can experience change in at least one mechanical characteristic when the target analyte is present in the sample. This change in a mechanical characteristic can be measured such that a mechanical signal is obtained, in addition to the optoplasmonic signal. The presence of the nanoparticle when the target analyte is present in the sample also produces an amplified mechanical signal due to the greater mass provided by the nanoparticle.

The mechanical element can be in the form of a microcantilever, a micropillar, a string resonator, a trampoline resonator, a rectangular cantilever, a triangular cantilever, a pyramidal cantilever, a blade cantilever, a membrane resonator, a plate resonator, a bridge, a hollow cantilever or a nanowire. In a particularly preferred embodiment, the substrate is arranged for acting as a mechanical element in the form of a microcantilever.

Furthermore, a change in any mechanical characteristic of the mechanical element can be measured for the purpose of detecting the presence of the target analyte in the sample. The change detected in the mechanical characteristic can be selected from, although it is not limited to, the position of a portion of the mechanical element, the vibration characteristic of the mechanical element, such as the vibration phase of the mechanical element, the vibration frequency of the mechanical element, the vibration amplitude of the mechanical element or the surface tension on a portion of the mechanical element or the changes in dissipation of the mechanical element.

The combination of the optical data obtained in step d) with the mechanical data of step e) of the present method provides an improved reliability of the method.

Finally, another objective of the invention is a device which can detect the enhanced optoplasmonic effect of the nanoparticles by means of the system of the invention or by combining the detection of such optoplasmonic effect with the analysis of the changes in the mechanical characteristics in the substrate.

More precisely, the device for surface inspection arranged for detecting the optoplasmonic effect in at least one nanoparticle of a system according to steps c) and d) of the method of the invention comprises:

- an electromagnetic radiation source arranged for generating at least one electromagnetic radiation beam;
- a first sensitive detector such as a dark-field microscope or a cross-polarization microscope arranged for receiving the electromagnetic radiation when it is reflected from or transmitted through the substrate for producing at least a first output signal in response to the scattering and/or extinction of said electromagnetic radiation;
- an electronic control system.

Additionally, in order to perform steps e) and f) of the method of the invention in which changes in the mechanical characteristics are measured when the target analyte is present in the sample, the device also comprises:

- a subsystem for detecting a change in a mechanical characteristic in the substrate, said subsystem comprising a second sensitive detector arranged for detecting a mechanical change in the substrate for producing at least a second signal in response to said mechanical change, specifically:
  - an illumination light or laser beam and a linear position sensitive photodetector (PSD) for recording the change in the mechanical characteristic on the substrate
  - an electronic control system;
  - scanning means for scanning the relative shift of said light or laser beam with respect to the substrate such that they scan the substrate with the light beam following instructions from the electronic control system;

and
  means for producing a final output signal based on the combination of first and second output signals of the first and second sensitive detectors.

DESCRIPTION OF A PREFERRED EMBODIMENT OF THE INVENTION

Figure 1:
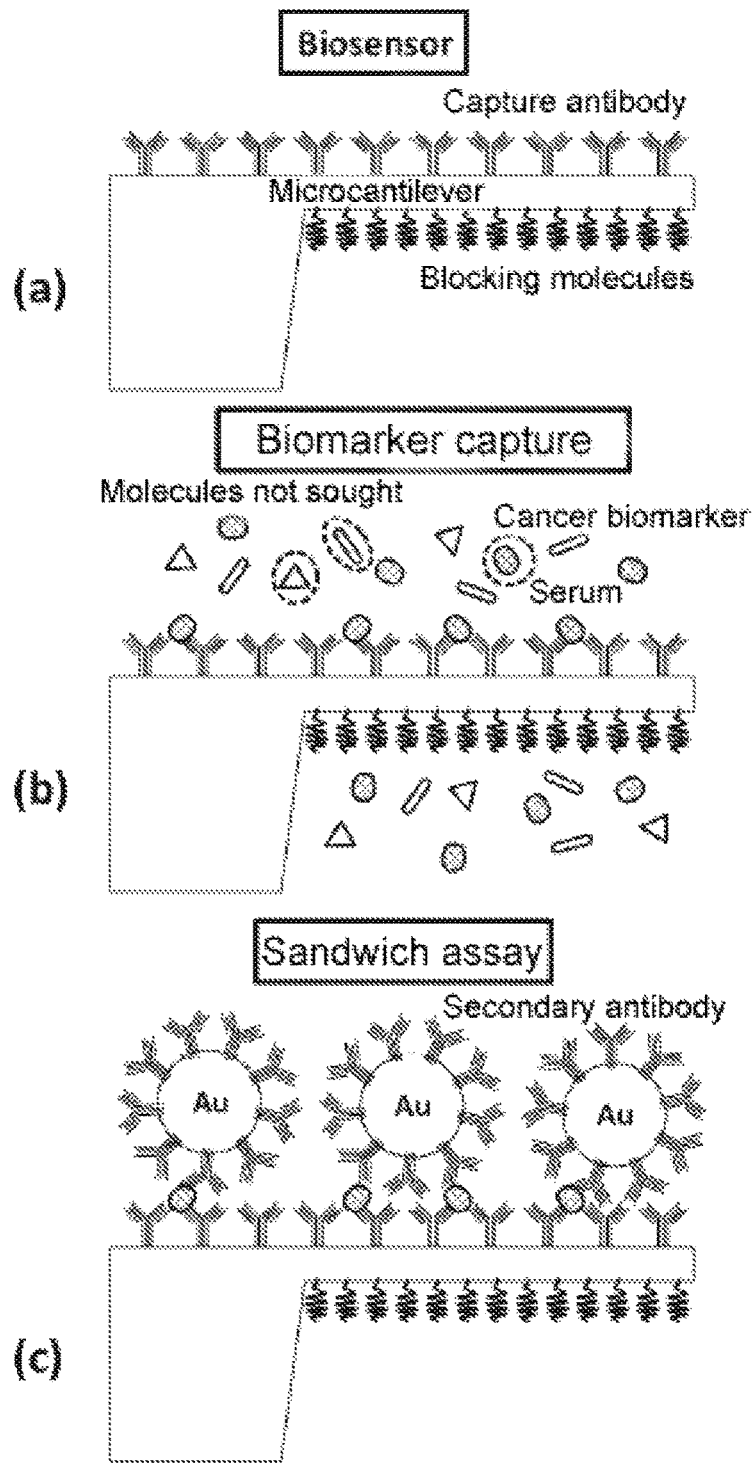
FIG. 1: Schematic depiction of the sandwich assay on the substrate in the form of a cantilever. (a) The cantilever is functionalized with capture antibodies. Functionalization comprises silanization, the binding of the antibody on the upper surface of the cantilever and blocking with polyethylene glycol to minimize non-specific interactions on the lower surface of the cantilever and gaps between the antibodies. (b) The cantilever is then immersed in the serum sample for binding the biomarker protein, if it is present, by immunoreaction with the capture antibodies (recognition element). (c) Finally, the immunoreactions are developed, exposing the cantilever to a primary antibody (detection element) which is bound to a gold nanoparticle 100 nm in diameter which recognizes a specific free region of the captured biomarker.
Figure 2:
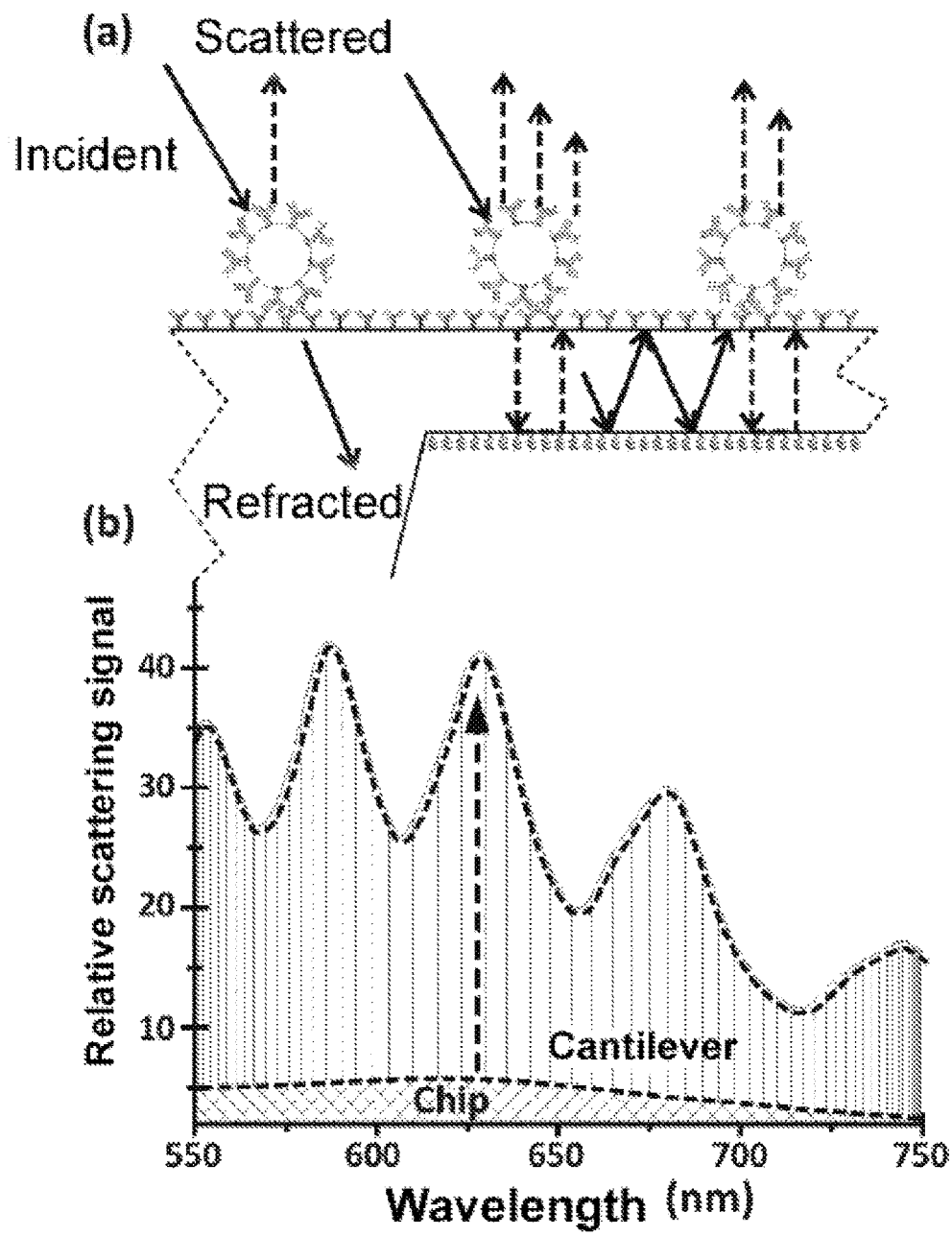
FIG. 2: Plasmonic detection of the CEA protein biomarker on the optical microcavity of the cantilever. (a) Diagrams illustrating the different pathways for the generation of the optical signal in the cantilever by means of multiple internal reflections. (b) Scattering spectra of the sandwich assay in chip and cantilever regions for the CEA detection assay. Scattering is normalized to scattering of the silicon chip. Coupling between dipolar plasmonic modes and individual modes of the microcavity of the cantilever leads to a dual effect, first plasmon-assisted scattering is enhanced by the optical cantilever cavity by almost one order of magnitude, and second the nanoparticle plasmon spectrum is individualized by the cantilever optical cavity modes.

As a concept test experiment for supporting the invention a sandwich immunoassay for detection of a cancer biomarker was performed. Detection of the carcinoembryonic antigen (CEA) was chosen as a model. First, a biofunctionalization method was applied to cantilevers with optimal recognition efficiency and ultra-low fouling capacity[33] (see FIG. 1a). The silicon cantilevers were 500 µm long, 100 µm wide and 1 µm thick. This biofunctionalization takes place in order to immobilize the receptor layer which recognizes and captures the cancer biomarker. After that, the biofunctionalized cantilever was immersed in the liquid sample for a specific period of time and at a fixed temperature in order to allow binding of the targeted biomarker to the capture antibodies immobilized on the cantilever surface (see FIG. 1b). After meticulous rinsing, the cantilever was exposed to a solution that contained the detection antibody bound to the nanoparticle which recognized and bound to a specific region of the captured surface biomarker (see FIG. 1c); the ideal time and temperature for the second recognition were also determined here. Basically, a sandwich assay involving two recognition steps was performed to enhance selectivity and amplify the response of the sensor. The detection antibody bound to a gold nanoparticle 100 nm in diameter which converted and amplified the biorecognition product into two detectable physical signals: (i) an increase in mass, and (ii) an increase in light scattering due to the plasmonic properties of the nanoparticle (see FIGS. 7a and 7b).

For these experiments, the protocol described in detail for capture antibody immobilization, biomarker detection and the sandwich assay was applied as described below.

Antibody Conjugation with Carboxyl-polymer Spherical Gold Nanoparticles

The primary monoclonal mouse anti-carcinoembryonic antigen 3C1 (MAb3C1) antibody was immobilized on the surface of carboxyl-polymer spherical gold nanoparticles 100 nm in diameter following the method provided by Nanopartz™. The sample was stored in the refrigerator at 4° C. until use.

Functionalization of the Cantilever and Activation of the Carboxyl Groups on the Surface Before surface functionalization, the cantilever arrays were cleaned with piranha solution ($3H_2SO_4:1H_2O_2$) (it should be noted that piranha solution is extremely corrosive and reactive as well as potentially explosive) for 15 minutes at room temperature (RT). The cantilevers were rinsed three times with Milli-Q water and dried under a nitrogen stream. The cantilevers were immersed in a 0.2% solution of (3-glycidyloxypropyl)trimethoxysilane in dry toluene overnight at room temperature. After that, the samples were washed with toluene, Milli-Q water and dried under $N_2$. A solution of 100 mM NTA in 50 mM carbonate buffer at pH 9.5 was prepared and the cantilevers were incubated overnight at 25° C. under gentle stirring. The cantilevers were then rinsed with 50 mM carbonate buffer at pH 9.5, Milli-Q water and dried under $N_2$. The carboxyl groups on the cantilever surface were activated by immersion in a mixed solution of 100 mM EDC and 150 mM sulfo-NHS, both dissolved in 10 mM MES at pH 5.5. The cantilevers were incubated for 45 minutes at 37° C. under gentle stirring. The samples were rinsed well with 10 mM MES.

Covalent and Oriented Immobilization of the Capture and Control Antibodies on the Cantilever Just after the step of surface activation, the antibody was immobilized on only the upper side of the cantilevers. A solution containing 50 µg/ml of the monoclonal mouse anti-carcinoembryonic antigen 3C6 (MAb3C6) capture antibody in 10 mM MES at pH 5.5 was prepared. The cantilevers were incubated for 2 hours at 37° C. After that, the samples were washed with 10 mM MES at pH 5.5 and incubated for 45 minutes at 37° C. with 10 mM sodium phosphate buffer at pH 8.0 with 0.3 M NaCl to desorb antibodies not covalently bound to the surface. For control experiments, anti-peroxidase (anti-HRP) antibody produced in rabbit was immobilized on the upper side of the cantilever surface instead of MAb3C6. The same antibody concentration and method applied to the covalent and oriented immobilization of MAb3C6 were used for the control samples. Before immobilization of the control antibody on the cantilevers, 1 ml of a solution of 4 mg/ml of anti-HRP in Milli-Q water was dialyzed overnight at 4° C. The concentration of the antibody solution after dialysis was determined using the Bradford assay [M. M. Bradford, M. M. *Analytical Biochemistry*, 1976, 72, 248-254]. A calibration curve was made using bovine serum albumin (BSA) as a protein pattern. The linearity range of the assay was from 5 µg/ml to 2500 µg/ml.

After immobilization of capture antibodies (MAb3C6) and control antibodies (anti-HRP) in a covalent and oriented mode and desorption of the antibodies not covalently bound to the surface, the cantilever surface was blocked to prevent non-specific adsorptions. The cantilevers were immersed in 1 mg/ml of (aminoethyl)polyethylene glycol (PEG) overnight at 4° C. After that, the samples were washed with MES at pH 5.5 with 0.05% Tween® 20 (pH 5.5).

Biomarker Recognition and Sandwich Assay

The cantilevers were incubated for 1 hour at 37° C. in CEA solutions with concentrations ranging from 1 pg/ml to 1 ag/ml in a solution of PBS with 0.05% Tween® 20 at pH 7.4 (PBST). In order to have meticulous control experiments, the solution CEA concentration used for these samples was 1 µg/ml. To simulate a real sample, CEA solutions with a concentration ranging from 100 fg/ml to 10 ag/ml in SBF were prepared and for the meticulous control experiments in SBF the concentration of CEA was maintained at 1 µg/ml. Right after that, the cantilevers were washed twice with PBST and once with PBS at pH 7.4. After that, the samples were rinsed with Milli-Q water and dried under an $N_2$ stream.

For the sandwich assay, the cantilevers were immersed in 1 µg/ml of a solution of spherical gold nanoparticles functionalized with the detection antibody (GNPs-MAb3C1) prepared in 10 mM MES with 0.05% Tween® 20 pH 5.5. The samples were incubated at 37° C. for 1 hour under gentle stirring, washed three times with MES with Tween, two times with MES, rinsed well with Milli-Q water and dried under an $N_2$ stream.

Biomarker recognition efficiency can be affected by the bioreceptor layer immobilized on the cantilever and also by the experimental conditions at which the recognition reaction takes place, such as temperature, pH and time. Strategies for immobilizing the bioreceptor layer must be optimized for each case; they can include the orientation and density of the receptors on the surface and blocking strategies to prevent non-specific interactions. For example, if the detection biomarker is a small protein, the strategy for immobilizing antibodies on the microcantilever surface, such as density and orientation, and the chosen blocking molecule will not be the same if the biosensor is now developed for detection of a bacterial cell, which is larger. Even when working only with antibodies, conditions can change; ideal conditions such as concentration, pH, time and temperature to be used must be determined and optimized. The immobilization and experimental conditions for analyte recognition must be customized for each case; however, the principle of the method described herein based on dual detection is still the same.

Optical measurements were taken using a commercial optical microscope in dark-field reflection mode (Axioskop 2 MAT equipped with AxioCam MRc 5 and bright-field/ dark-field Zeiss 50x EC Epiplan Neofluor® lenses from Zeiss—Oberkochen, Germany). The chip and cantilever surfaces were observed after the step of CEA recognition on the cantilever and after the sandwich assay (binding of the nanoparticles functionalized with the detection antibody).

Figure 3:
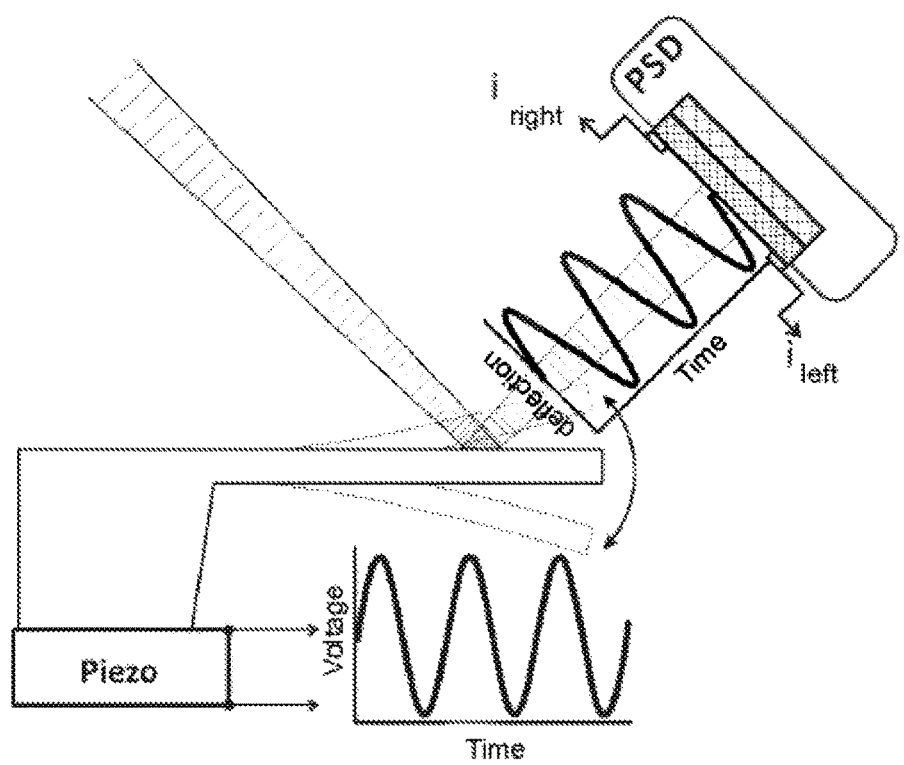
FIG. 3: Diagrams of the method of deflection of the optical ray for measuring vibration of the cantilever. A laser beam is focused on the region of the free end of the cantilever. The deflection of the beam reflected due to vibration of the cantilever is measured by a linear position sensitive photodetector (PSD). A frequency generator scans the frequency by exciting a piezoelectric actuator located below the base of the cantilever array. The vibration amplitude with respect to frequency is adjusted to the harmonic oscillator model to derive the resonance frequency and the quality factor of the cantilever.

The resonance frequency was obtained from the cantilever actuated vibration which is detected optically by means of the simple optical cantilever method[35] (see FIG. 3). The resonance frequency of the fundamental vibration mode of the cantilever is measured in air before and after exposing the cantilever to the gold nanoparticles functionalized with the primary antibody.

Figure 4:
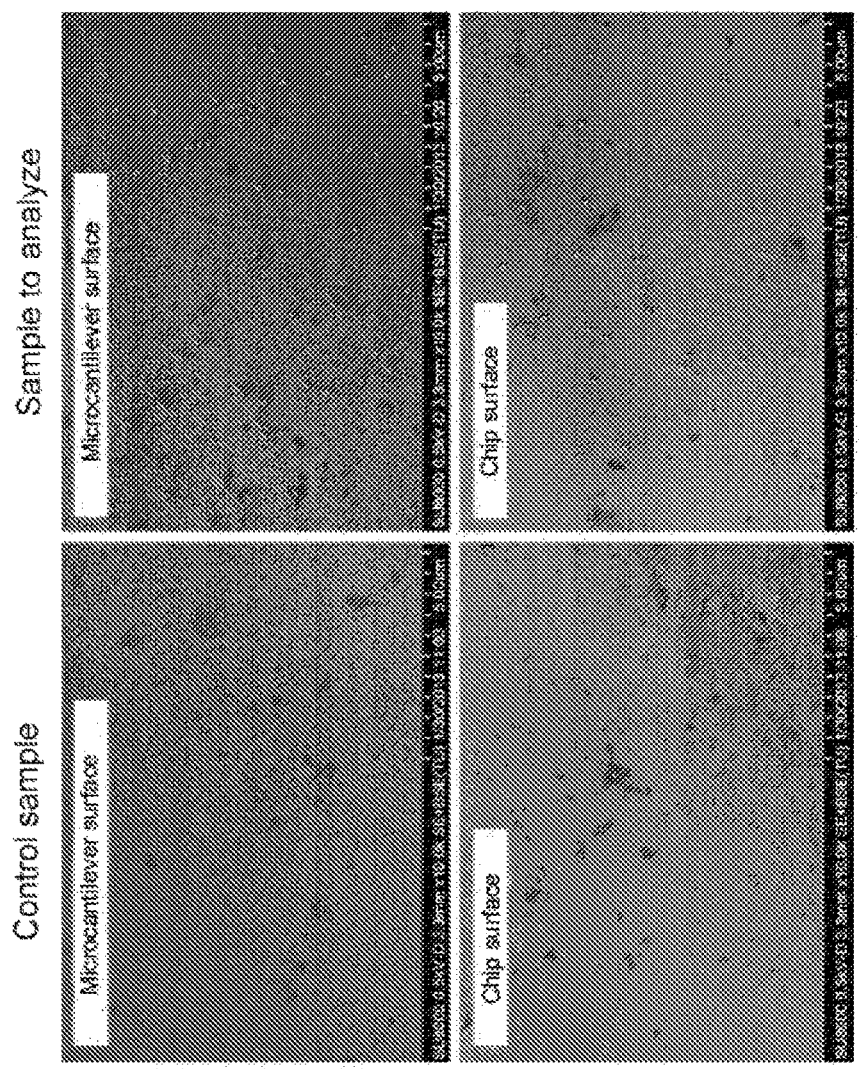
FIG. 4: Scanning electron microscope (SEM) images of a region of the cantilever that complies with the design leading to the enhanced plasmonic effect (microcantilever surface) and chip having dimensions not leading to the enhanced plasmonic effect, both after the sandwich assay in a control experiment and in a detection assay for the detection of 1 pg/ml of CEA in serum. The cantilever surface and the chip surface show the same average amount of nanoparticles.
Figure 5:
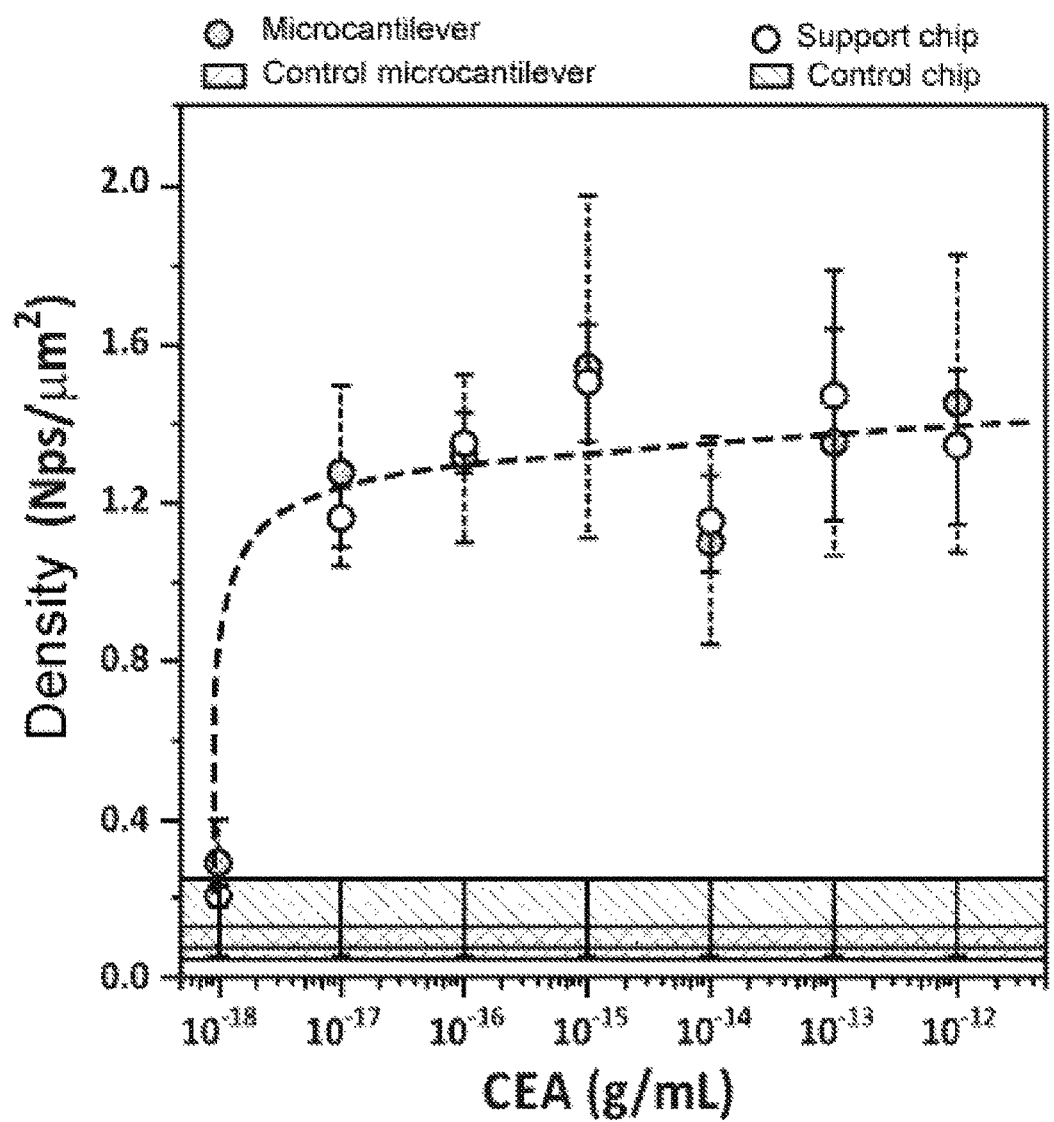
FIG. 5: Density of nanoparticles on the microcantilevers and chip in buffer measured with a scanning electron microscope and using a signal-contrast based algorithm implemented in Matlab software.

The samples used in the experiments for the concept test were analyzed by scanning electron microscopy (SEM) as illustrated in FIG. 4. At least 100 images were taken of the cantilever and the chip for each detected CEA concentration and both surfaces showed the same nanoparticle density (FIG. 5). The information obtained from the SEM images will be used to support the results found for the optical and mechanical measurements.

Figure 6:
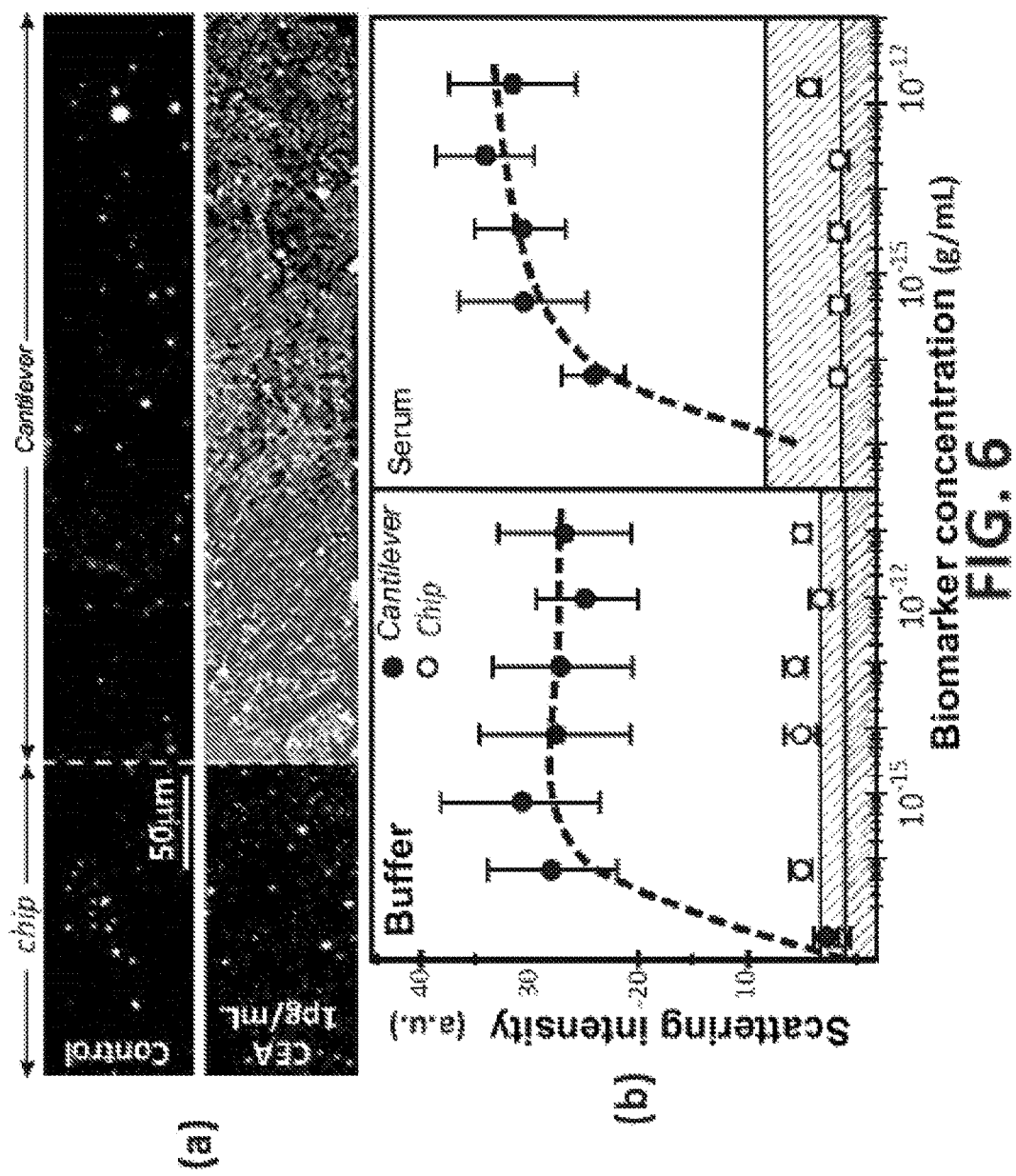
FIG. 6: Plasmonic detection of the CEA protein biomarker. (a) Dark-field optical images of the cantilever after the step of recognition with the antibodies bound to the nanoparticles for a meticulous control experiment and for the CEA detection assay with a sample of 1 pg/ml in phosphate-buffered saline solution. The scattering signal is insignificant in the control experiment, whereas it is significantly higher in the microcantilever region in the detection assay. The microcantilever acts like an optical cavity, whereas scattering in the pre-clamping region of the chip is low and cannot be used for discriminating the presence of CEA in the sample. (b) Mean scattering signal in the microcantilever and the chip with respect to the buffer and serum CEA concentration. The signal is obtained from a rapid inspection of the cantilevers with a simple commercial optical microscope and dark-field lens with low magnification. The cantilever data is compared with the chip data to evaluate the effect of the optical cantilever cavity. Scattering for the control experiments in the cantilever and chip regions are represented as discontinuous regions representing the standard deviation of the data.

FIG. 6a shows the dark-field images of the chip region for a control experiment and for a detection experiment with 1 pg/ml of CEA in PBS. The scattering signal is negligible in the control experiment. In the case of the CEA detection assay, a negligible increase in scattering is observed in the chip region; the chip region has dimensions outside the rules of design for the substrate in the invention, thereby not leading to the enhanced plasmonic effect, whereas the bound nanoparticles make the area of the cantilever bright, since the cantilever complies with the design leading to the enhanced plasmonic effect.

The mean scattering signal obtained from the dark-field images is represented in FIG. 6b depending on the buffer or serum CEA concentration. The limit of detection found for the experiments performed in buffer medium is 0.1 fg/ml. The scattering signal in the cantilever is about 6 times the signal in the chip, showing the increases in the optical signal due to the designed substrate. The resonant enhancement of the scattering signal has a determination function in CEA detection at ultra-low serum concentrations. Therefore, the scattering signal in the chip is based on the region obtained in the control experiments for CEA concentrations from 0.1 fg/ml to 100 fg/ml. Surprisingly, the enhancement of the scattering signal induced by the cantilever cavity allows discrimination of concentrations of only 0.1 fg/ml.

Figure 7:
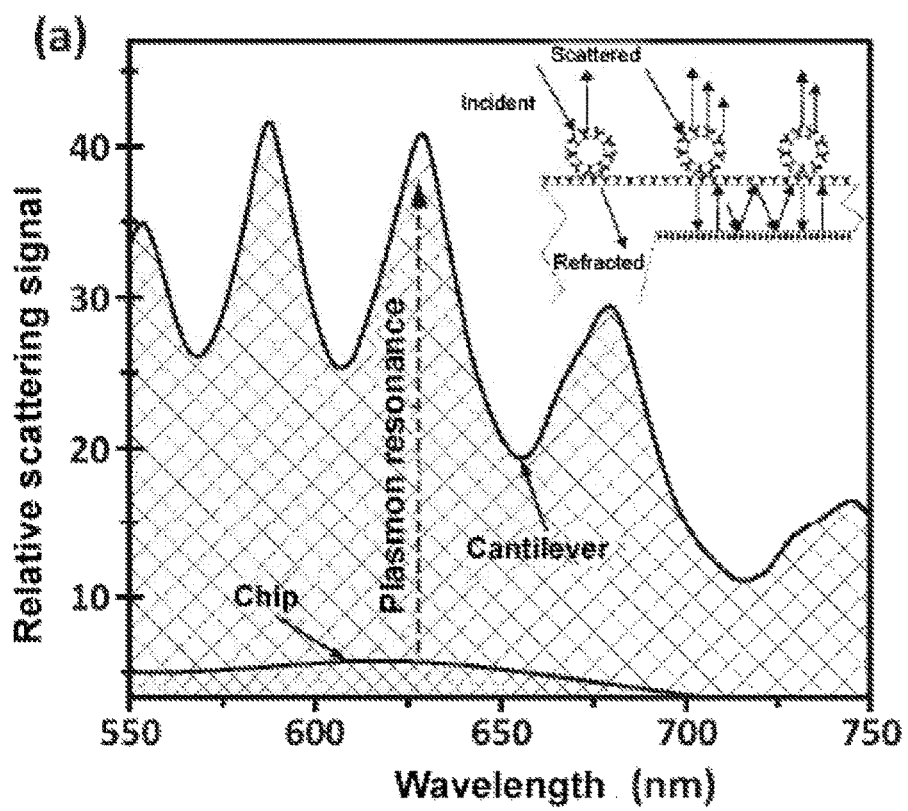
FIG. 7: (a) Scattering spectra of the effect of the nanoparticles bound on the chip having dimensions not leading to the enhanced plasmonic effect, and cantilever regions complying with the design leading to the enhanced plasmonic effect. Scattering is normalized to scattering of a raw silicon chip. The box illustrates the different pathways for generating the signal scattered in the cantilever by means of multiple internal reflections (also depicted in FIG. 2.) (b) Diagrams of the effect of the nanoparticle mass load on the resonance frequency of the cantilever. The reduction resulting from the resonance frequency is proportional to the increase in mass.
Figure 7:
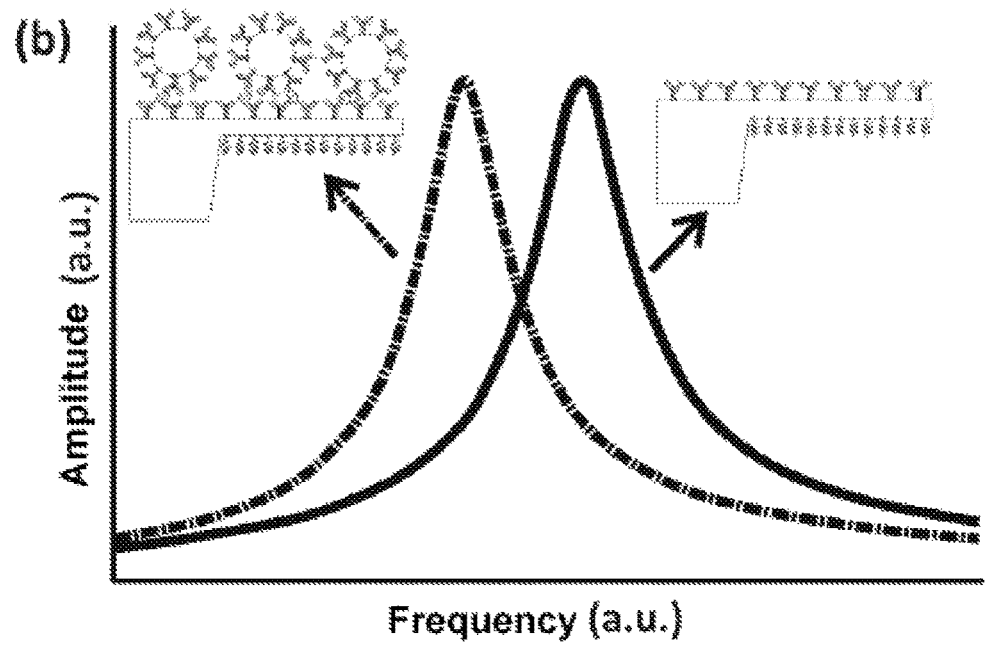

The bright appearance of the cantilever is related to its effect as an optical cavity, as outlined in FIG. 7a. If the light interacts with a nanoparticle on the chip of the cantilever (a support that does not comply with the rules of design of the objective of the invention), the scattered light that is picked up is given only by the backscattering from the separating surface between the environmental medium and the raw substrate. If the nanoparticle is on the cantilever, in addition to the backscattering observed in the raw support chip, multiple pathways help to enhance scattering by a single nanoparticle spectacularly enhancing the backscattering signal measured. One pathway involves amplification of the light scattered by the nanoparticle towards the cantilever by multiple reflections, producing multiple scattering methods. A second pathway encompasses the methods in which the light hitting the cantilever regions between nanoparticles experience multiple reflections in the optical cantilever cavity, causing a cascade of scattering interactions in the nanoparticle site.

Figure 8:
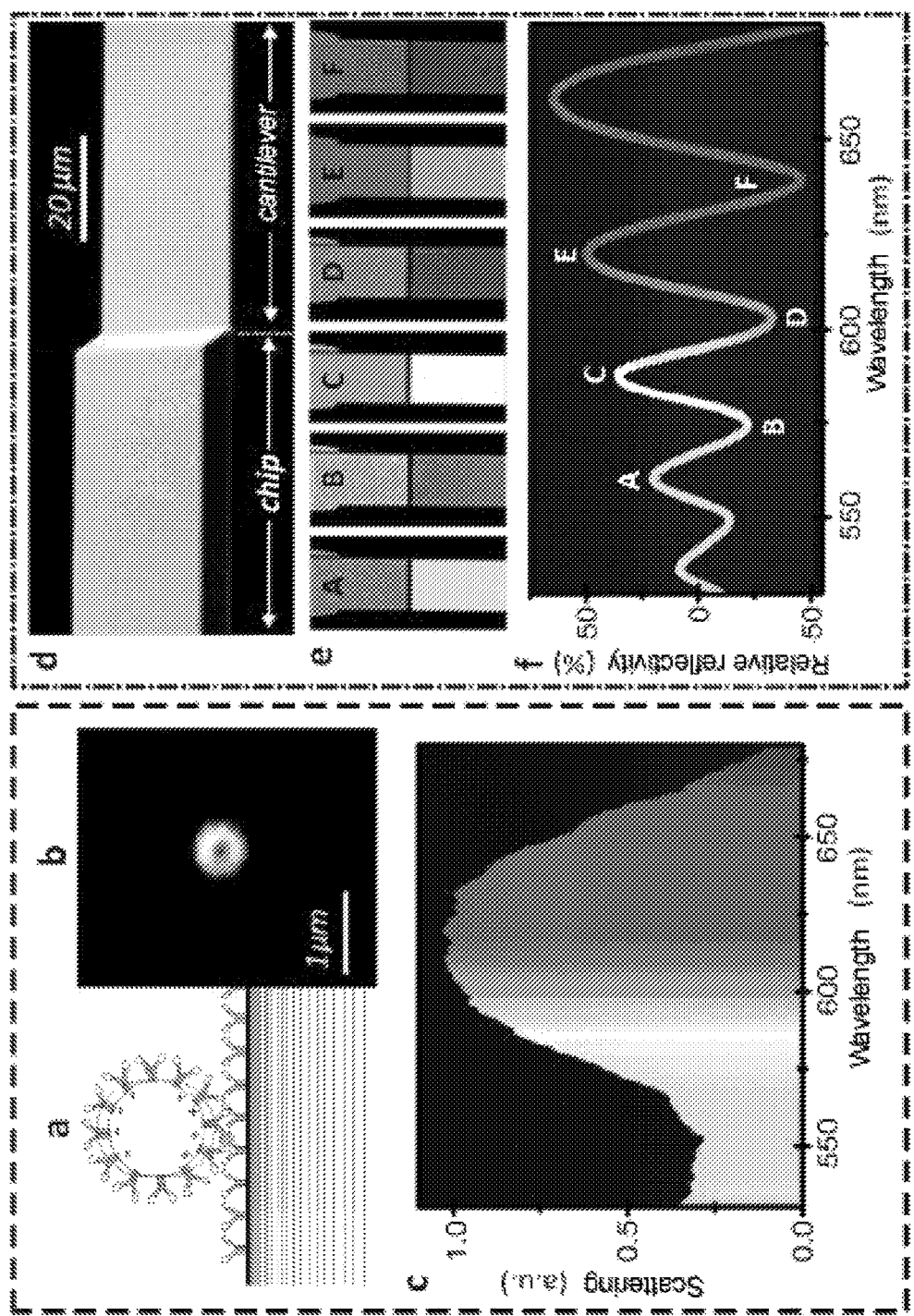
FIG. 8: Nanoparticle plasmon resonance and optical cantilever cavity. (a) The gold nanoparticles used in the sandwich assay characterize plasmon resonances associated with collective electron oscillations in the nanoparticle. These resonances give rise to enhanced scattering and absorption that are close to the optical resonance frequency. (b) Dark-field optical image of a single nanoparticle 100 nm in diameter after performing a sandwich assay on a silicon substrate. The gold nanoparticle has the very well-known Airy pattern due to light diffraction. (c) Scattering spectra taken of a 20×20 µm² area with a single nanoparticle. (d) Scanning electron microscopy image showing the border between the chip, 6 µm thick, and the cantilever, 1 µm thick. The thickness of the cantilever makes the light be able to effectively bounce around multiple times between opposing sides of the cantilever which give rise to an enhancement of the optical reflectivity at wavelengths in which constructive interference occurs, and in contrast, a suppression of reflectivity for wavelengths in which destructive interference occurs. (e) Bright-field images of the cantilever and chip regions showing cantilever reflectivity modulation with the illumination wavelength in the visible spectrum region. Chip reflectivity modulation is insignificant. (f) Relative reflectivity in the cantilever with respect to the chip.

In order to determine the coupling between the optical cavity and the plasmon response, the spectral response of the scattering in the cantilever and the support chip was analyzed. The spectra showed the resonant enhancement of plasmon-assisted scattering of the optical cantilever cavity by almost one order of magnitude. The methods of multiple reflections in the cantilever cavity give rise to modulation of the scattering signal with the wavelength, which is reminiscent of the reflectivity modulation shown in FIG. 8.

Figure 9:
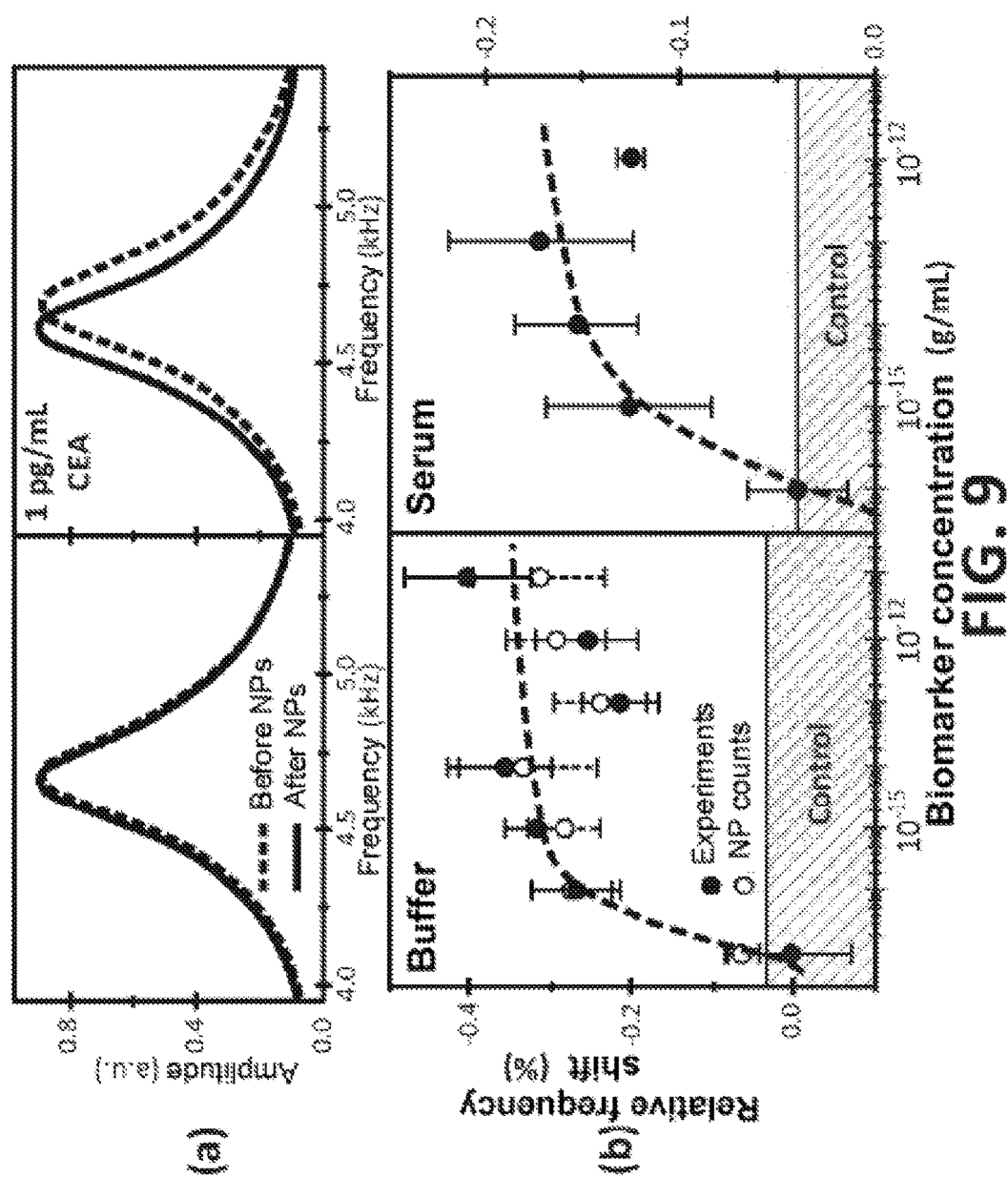
FIG. 9: Mechanical detection CEA protein biomarker. (a) Mechanical resonance frequency of a silicon cantilever before and after the step of recognition with the antibodies bound to nanoparticles for a control experiment and for a CEA detection assay (1 pg/ml in PBS). Measurements were taken in air at room temperature. The fundamental resonance frequency and the quality factors of the uncoated cantilevers were 4.8±0.5 kHz and 5.5±0.5, respectively. (b) Relative resonance frequency shift of the fundamental vibration mode with respect to the buffer and serum sample biomarker concentration (red symbols). The lines are a guide for the eyes. The frequency shifts measured in buffer solution are compared with the predicted theoretical frequency shift of the distribution of nanoparticles on the cantilever obtained by scanning electron microscopy. The good match confirms that the frequency shift occurs based on the nanoparticle mass load. The frequency shift for control experiments is represented as a discontinuous region representing the standard deviation of the data.

FIG. 9 shows the mechanical frequency response of the cantilever due to the mass added by antibody-coated nanoparticles binding thereto. Mechanical resonance was measured by an instrument with a laser beam deflection method as depicted in FIG. 3 for the reading. FIG. 9a shows the mechanical resonance frequency peak before and after the step of nanoparticle recognition in buffer medium for the control experiment and for 1 pg/ml of CEA. The mechanical resonance peaks before and after exposure of the control cantilever to the solution containing the CEA biomarkers show negligible differences. A significant shift of the mechanical resonance peak to lower frequencies is observed in the CEA detection assay. The mechanical resonance frequency shifts with respect to CEA concentration are depicted in FIG. 9b for purified buffer (left) and solutions in serum (right). The mechanical resonance shift in buffer solution are shown in FIG. 9b (left) together with the biological base noise base determined in the control assays. The experimental data shows an excellent coincidence with the theoretical prediction based on the mass of the nanoparticles bound to the cantilever which the authors of the present invention have evaluated by SEM. The limit of detection in these calibration curves is 0.1 fg/ml. The limit of detection increases by one order of magnitude when the assays are performed in serum due to the huge amount of non-specific competitive interactions between plasma biomolecules and the cantilever surface.

Figure 10:
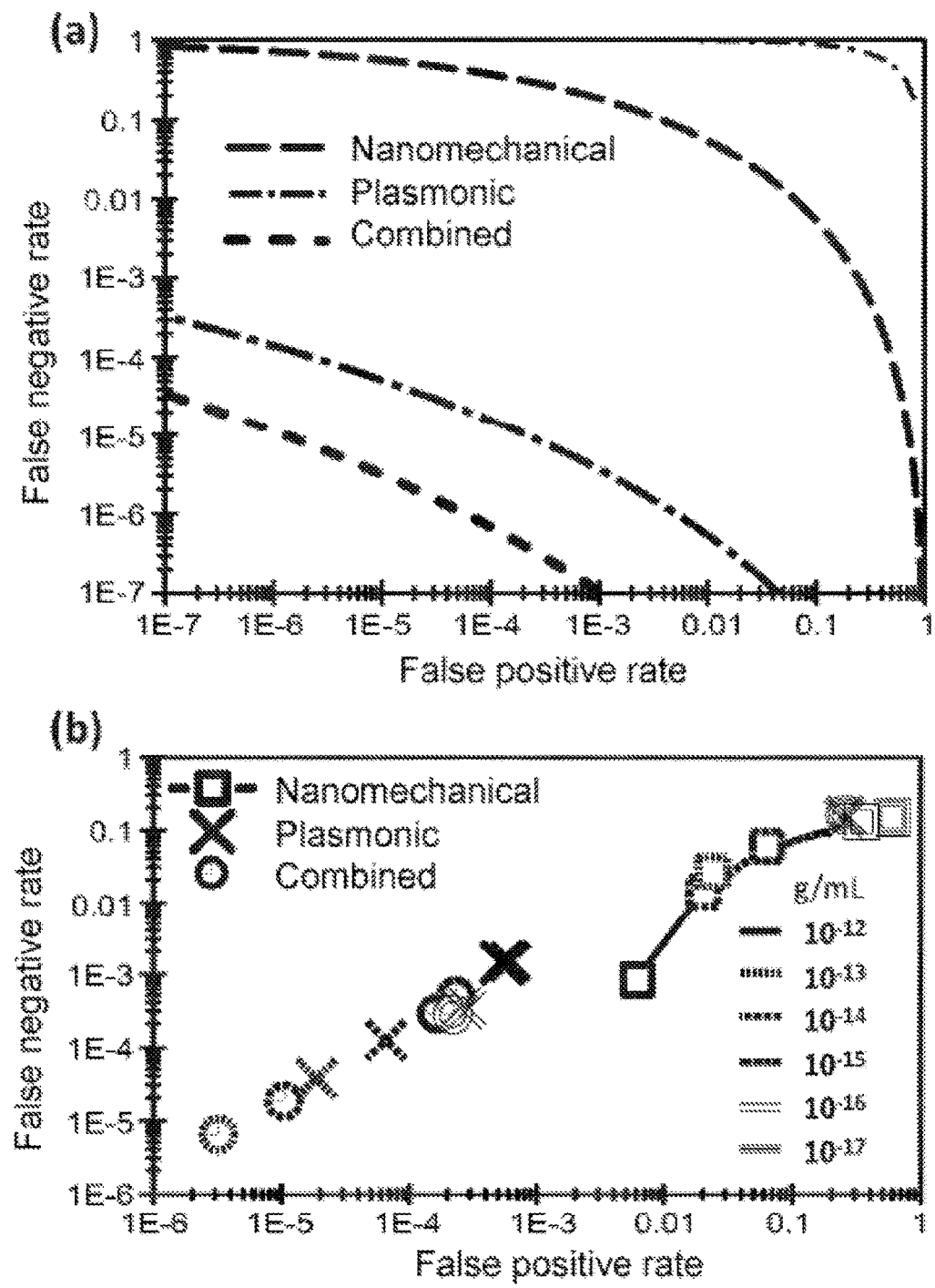
FIG. 10: (a) DET curves for a concentration of 10 fg/ml using nanomechanical and plasmonic signals and an optimal linear combination thereof. (b) False negative rate with respect to the false positive rate for each transduction mechanism and for a hybrid method using an optimal linear combination of the scattering and mechanical resonance frequency shift signals. The colors indicate the target concentration.
Figure 11:
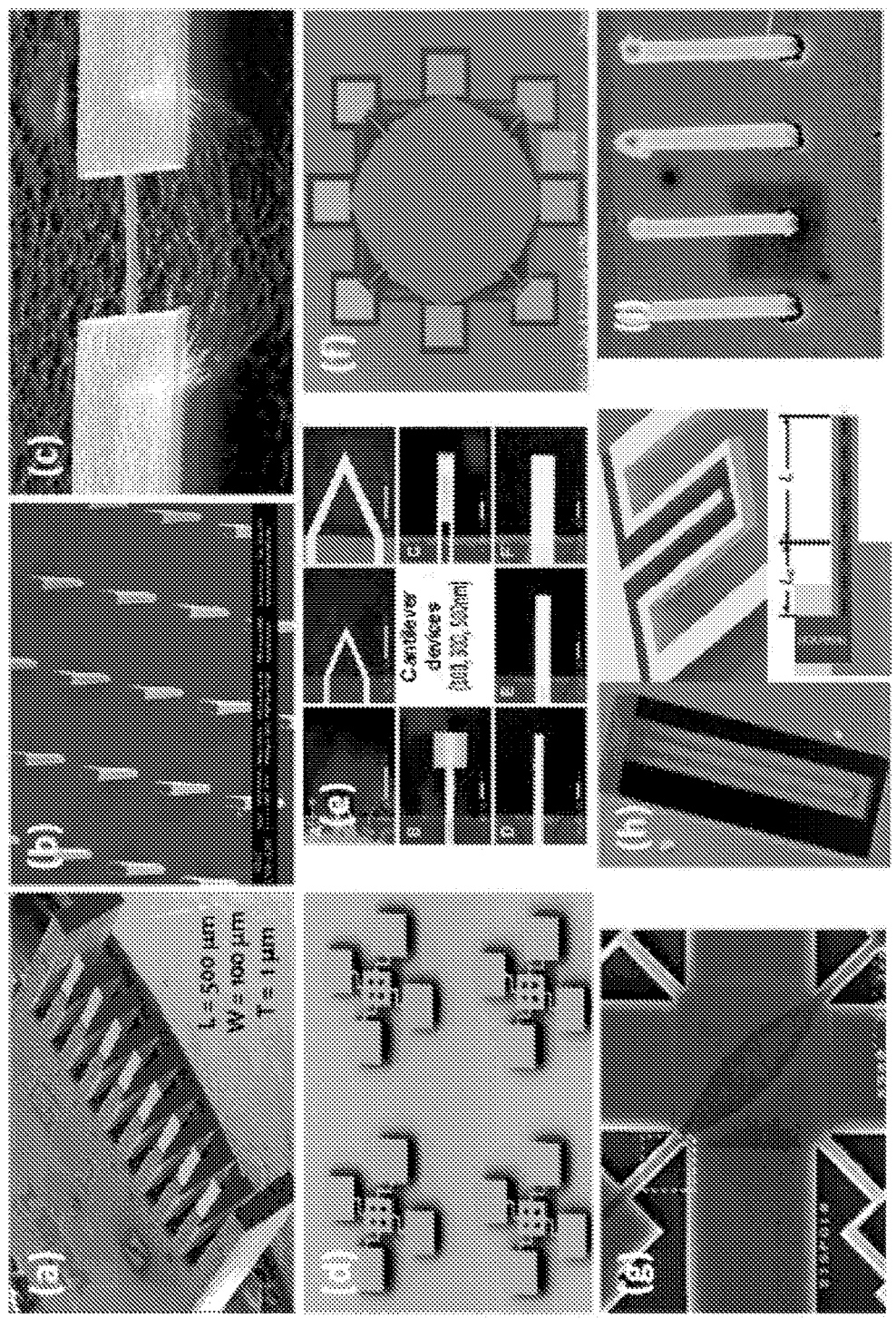
FIG. 11: Examples of different forms for the substrate of the system (a) commercial microcantilevers, (b) micropillar resonators, (c) string resonator, (d) trampoline resonators, (e) rectangular, triangular and blade cantilevers, (f) membrane resonators, (g) plate resonators, (h) SEM image of a hollow cantilever and schematic depiction, (i) nanowire.
Figure 12:
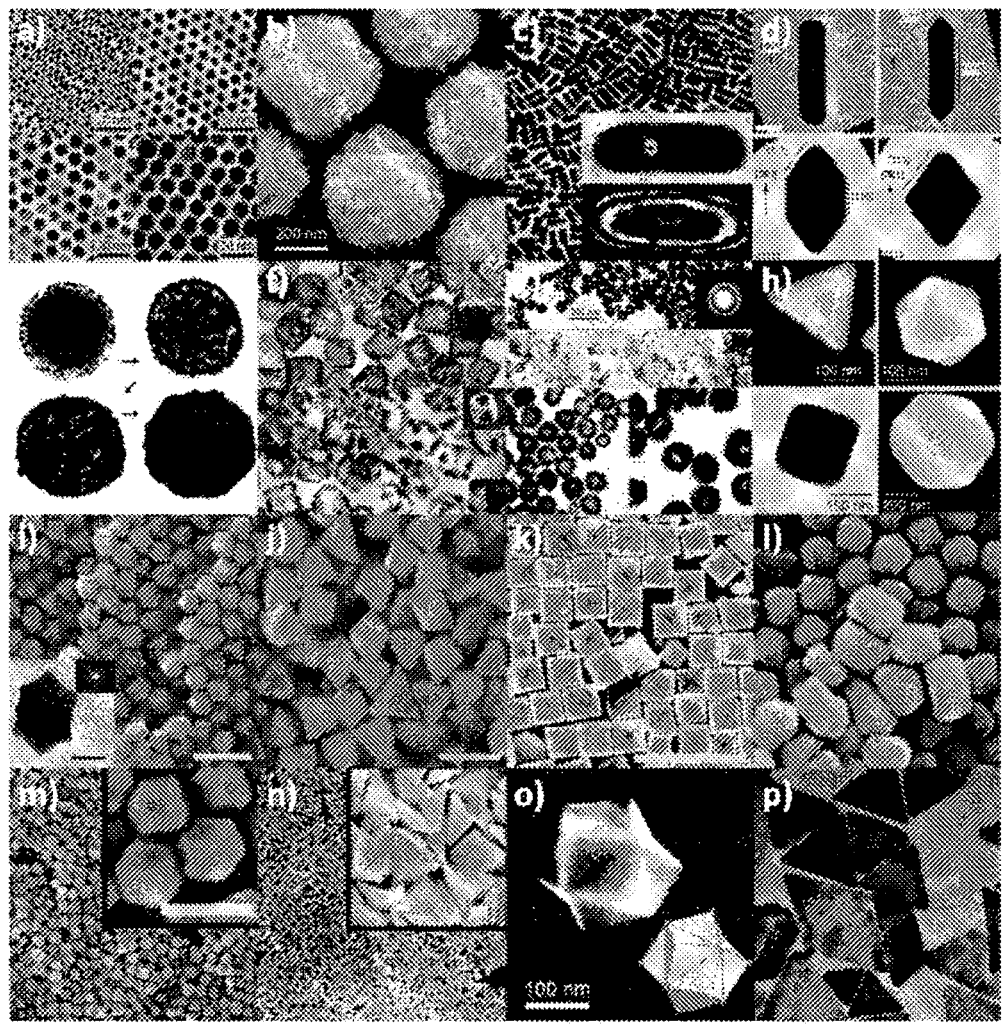
FIG. 12: Gold nanoparticles of various sizes and shapes useful in the system of the invention. Small nanospheres (a) and large nanospheres (b), (c) nanorods, (d) pointed nanorods, (e) nanoshells, (f) nanocages/frames, (g) hollow nanospheres, (h) tetrahedra/octahedra/cubes/icosahedra, (i) rhombic dodecahedra, (j) octahedra, (k) concave nanocubes, (l) tetrahexahedra, (m) rhombic dodecahedra, (n) obtuse triangular bipyramids, (or) trisoctahedra and (p) nanoprisms.

The fact that the optical technique reaches a higher limit of detection than that obtained with the mechanical measurement does not mean that it is a better biosensor. A statistical analysis of the reliability of pure mechanical and optical sensors indicates that both biosensors have similar performances, but the combination of the two transduction mechanisms led to a dual biosensor with an improved performance as can be seen in FIG. 10.

Statistical Study of the Reliability of the Optomechanical Plasmonic Sensor (Hybrid Signal)

The sensitivity and specificity of a diagnostic test are a function of a chosen threshold value. Changing the threshold value such that sensitivity increases will decrease specificity, and vice versa. The receiver operating characteristic (ROC) curve is a graph of all the sensitivity/specificity pairs resulting from continuously changing the decision threshold with respect to the complex range of results observed. This is a graph of the true positive (or sensitivity) rate on the y-axis and the true negative (specificity 1) rate on the x-axis. The true positive rate (TPR) is the probability that a case of disease is correctly classified and the true negative rate (TNR) is the probability that a normal true case is correctly classified. The ROC curve can also be used to compare the performance of two or more diagnostic tests[7,8]. An alternative to the ROC curve is the detection error tradeoff (DET) graph, representing the false negative rate (detections that are missed) with respect to the false positive rate (false alarms) on the logarithmic x and y axes. This alternative takes up a larger graph area in the region of interest, i.e., the region with the minimum false rate. The DET graph is made by superimposing a normal distribution determined by the experimentally obtained mean value and standard deviation. FIG. 10a shows DET curves for a concentration of 10 fg/ml by the plasmonic and nanomechanical transduction methods. The dotted-dashed line corresponds with a random parameter. Both transduction methods provide DET curves that are far below this non-discrimination curve. The optimal value of the threshold signal is that which offers a minimum in the distance between the DET curve and the origin. The case in which the signal of the authors of the present invention is a combination of the scattering intensity and the mechanical resonance frequency shift is now considered[7]. The linear combination is optimized by minimizing the minimum distance between the DET curve and the origin. Therefore, as a result of the dual signal, the false detection rate in the detection of the authors of the present invention is always enhanced as shown in FIG. 10a. The enhancement in reliability is modest for the lower concentrations as can be seen in FIG. 10b, in which plasmonic transduction is clearly greater than nanomechanical transduction. However, as the concentration increases, reliability of both transduction methods becomes comparable, and optimization by a linear combination of both signals is clearly advantageous (see the sphere symbols in FIG. 10b).

REFERENCES

1. D'Orazio, P. Biosensors in clinical chemistry-2011 update. *Clinica Chimica Acta* 412, 1749-1761 (2011).
2. Tothill, I. E. 55-62 (Elsevier).
3. Justino, C. I. L., Rocha-Santos, T. A. & Duarte, A. C. Review of analytical figures of merit of sensors and biosensors in clinical applications. *TrAC Trends in Analytical Chemistry* 29, 1172-1183 (2010).
4. Fan, X. et. al. Sensitive optical biosensors for unlabeled targets: A review. *Analytica chimica acta* 620, 8-26 (2008).
5. Wang, J. Carbon-nanotube based electrochemical biosensors: A review. *Electroanalysis* 17, 7-14 (2005).
6. Wang, J. Electrochemical biosensors: Towards point-of-care cancer diagnostics. *Biosensors and Bioelectronics* 21, 1887-1892 (2006).
7. Wang, J. Amperometric biosensors for clinical and therapeutic drug monitoring: a review. *Journal of pharmaceutical and biomedical analysis* 19, 47-53 (1999).
8. Stern, E. et. al. Label-free biomarker detection from whole blood. *Nature nanotechnology* 5, 138-142 (2009).
9. Duan, X. et. al. Quantification of the affinities and kinetics of protein interactions using silicon nanowire biosensors. *Nature nanotechnology* 7, 401-407 (2012).
10. Zheng, G., Gao, X. P. A. & Lieber, C. M. Frequency domain detection of biomolecules using silicon nanowire biosensors. *Nano Letters* 10, 3179-3183 (2010).
11. Dixon, M. C. Quartz crystal microbalance with dissipation monitoring: enabling real-time characterization of biological materials and their interactions. *Journal of biomolecular techniques: JBT* 19, 151 (2008).
12. Lange, K., Rapp, B. E. & Rapp, M. Surface acoustic wave biosensors: a review. *Analytical and bioanalytical chemistry* 391, 1509-1519 (2008).
13. O'sullivan, C. & Guilbault, G. Commercial quartz crystal microbalances-theory and applications. *Biosensors and Bioelectronics* 14, 663-670 (1999).
14. Arlett, J., Myers, E. & Roukes, M. Comparative advantages of mechanical biosensors. *Nature nanotechnology* 6, 203-215 (2011).
15. Boisen, A. & Thundat, T. Design & fabrication of cantilever array biosensors. *Materials Today* 12, 32-38 (2009).
16. Datar, R. et. al. Cantilever sensors: nanomechanical tools for diagnostics. *MRS bulletin* 34, 449-454 (2009).

17. Boisen, A., Dohn, S., Keller, S. S., Schmid, S. & Tenje, M. Cantilever-like micromechanical sensors. *Reports on Progress in Physics* 74, 036101 (2011).
18. Fritz, J. Cantilever biosensors. *Analyst* 133, 855-863 (2008).
19. Raiteri, R., Grattarola, M., Butt, H. J. & Skladal, P. Micromechanical cantilever-based biosensors. *Sensors and Actuators B: Chemical* 79, 115-126 (2001).
20. Waggoner, P. S. & Craighead, H. G. Micro- and nanomechanical sensors for environmental, chemical, and biological detection. *Lab Chip* 7, 1238-1255 (2007).
21. Kathryn M. Mayer, Jason H. Hafner, Localized Surface Plasmon Resonance Sensors, Chemical Reviews 111, 3828-3857 (2011)
22. Roberto de la Rica, Molly M. Stevens, Plasmonic ELISA for the ultrasensitive detection of disease biomarkers with the naked eye, Nature Nanotechnology 7, 821-824 (2012)
23. Jwa-Min Nam, C. Shad Thaxton, Chad A. Mirkin, Nanoparticle-Based Bio-Bar Codes for the Ultrasensitive Detection of Proteins, Science 301, 1884-1886 (2003)
25. Dong et. al., Two types of nanoparticle-based bio-barcode amplification assays to detect HIV-1 p24 antigen, Virology Journal 9, 180 (2012)
26. Elghanian R, Storhoff J J, Mucic R C, Letsinger R L, Mirkin C A, Selective colorimetric detection of polynucleotides based on the distance-dependent optical properties of gold nanoparticles, Science 277, 1078-81 (1997)
27. James J. Storhoff, Robert Elghanian, Robert C. Mucic, Chad A. Mirkin, Robert L. Letsinger, One-Pot Colorimetric Differentiation of Polynucleotides with Single Base Imperfections Using Gold Nanoparticle Probes, J. Am. Chem. Soc., 120, 1959-1964 (1998).
28. T. Andrew Taton, Chad A. Mirkin, Robert L. Letsinger, Scanometric DNA Array Detection with Nanoparticle Probes, Science 289, 1757-1760 (2000).
29. Robert Jenison, Shao Yang, Ayla Haeberli, Barry Polisky, Interference-based detection of nucleic acid targets on optically coated silicon, Nature Biotechnology 19, 62-65 (2001).
30. Goluch E D1, Nam J M, Georganopoulou D G, Chiesl T N, Shaikh K A, Ryu K S, Barron A E, Mirkin C A, Liu C., A bio-barcode assay for on-chip attomolar-sensitivity protein detection, Lab Chip. 6, 1293-9 (2006).
31. Waggoner, P. S., Varshney, M. & Craighead, H. G. Detection of prostate specific antigen with nanomechanical resonators. Lab Chip 9, 3095-3099 (2009).
32. Nair, P. R. & Alam, M. A. Theory of "Selectivity" of label-free nanobiosensors: A geometro-physical perspective. Journal of applied physics 107, 064701-064701-064706 (2010).
33. Priscila M. Kosaka, Javier Tamayo, José J. Ruz, Sara Puertas, Ester Polo, Valeria Grazu, Jesús M. de la Fuente and Montserrat Calleja. Tackling Reproducibility in Microcantilever Biosensors: A Statistical Approach for Sensitive and Specific End-point detection of Immunoreactions, Analyst 138, 863-872 (2013).
34. Varshney M, Waggoner P S, Tan C P, Aubin K, Montagna R A, Craighead H G., Prion protein detection using nanomechanical resonator arrays and secondary mass labeling, Anal Chem. 80, 2141-8 (2008).
35. Javier Tamayo, Valerio Pini, Prisicila Kosaka, Nicolas F Martinez, Oscar Ahumada, Montserrat Calleja, Imaging the surface stress and vibration modes of a microcantilever by laser beam deflection microscopy, Nanotechnology, 23, 315501 (2012).

The invention claimed is:
1. A system for biodetection applications comprising:
a. a substrate of dielectric material having at least one surface functionalized with a recognition element which can bind specifically to a target analyte, the dielectric material being surrounded by a surrounding material wherein the substrate acts as a mechanical resonator and optical cavity; and
b. at least one nanoparticle with plasmonic properties which comprises at least one detection element bound thereto and which can bind specifically to the target analyte in a sandwich-type arrangement,
characterized in that:
the substrate of dielectric material has a thickness between 0.1 µm and 5 µm and an extinction coefficient less than 0.3,
the nanoparticle has at least one of its dimensions with a size of 2 nm to 300 nm,
the ratio between the refractive index of the dielectric material and the surrounding material is greater than 1.1, and
in that the system detection is performed by an optoplasmonic detection of an enhanced plasmonic effect.
2. The system according to claim 1, wherein the dielectric material is selected from quartz, silicon, silicon nitride, silicon carbide, graphene, polymers and hydrogels.
3. The system according to claim 1, wherein the substrate is in the form of a microcantilever, a micropillar, a string resonator, a trampoline resonator, a rectangular cantilever, a triangular cantilever, a pyramidal cantilever, a blade cantilever, a membrane resonator, a plate resonator, a bridge, a hollow cantilever or a nanowire.
4. The system according to claim 1, wherein the substrate is functionalized with a recognition element selected from an antibody, a receptor, a peptide, a protein, a carbohydrate, a nucleic acid, a cell, a microorganism or a part thereof.
5. The system according to claim 1, wherein the detection element is selected from an antibody or a nucleic acid molecule.
6. The system according to claim 1, wherein the nanoparticle is a gold nanoparticle, a silver nanoparticle or a nanoparticle of plasmonic metamaterial.
7. The system according to claim 1, wherein the nanoparticle has a structure selected from the group of nanospheres, nanorods, pointed nanorods, nanoshells, nanocages/frames, hollow nanospheres, tetrahedra, octahedra, cubes, icosahedra, rhombic dodecahedra, concave nanocubes, tetrahexahedra, obtuse triangular bipyramids, trisohectahedra and nanoprisms.
8. The system according to claim 1, wherein the substrate has a transmittance index comprised between 0.01 and 1 and/or a reflectance index comprised between 0.01 and 1.
9. A biosensor comprising the system according to claim 1.
10. A biosensor arranged in the form of an array comprising multiple systems according to claim 1, each system comprising a substrate designed for detecting a different target analyte or different concentrations of the same analyte.
11. A device for surface inspection arranged for detecting an optoplasmonic effect in at least one nanoparticle, said device comprising:
the system according to claim 1,
an electromagnetic radiation source arranged for generating at least one electromagnetic radiation beam;

a first sensitive detector arranged for receiving the electromagnetic radiation when it is reflected from or transmitted through the substrate for producing at least a first output signal in response to the scattering and/or extinction of said electromagnetic radiation; and an electronic control system.

12. The device according to claim 11, wherein the device further comprises:

a subsystem for detecting a change in a mechanical characteristic in the substrate, said subsystem comprising a second sensitive detector arranged for detecting a mechanical change in the substrate for producing at least a second signal in response to said mechanical change; and means for producing a final output signal based on the combination of first and second output signals of the first and second sensitive detectors.

13. The device according to claim 12, wherein said detection subsystem comprises:

an illumination light or laser beam and a linear position sensitive photodetector for recording the change in the mechanical characteristic on the substrate;

an electronic control system;

scanning means for scanning the relative shift of said light or laser beam with respect to the substrate such that they scan the substrate with the light beam following instructions from the electronic control system.

* * * * *